(12) United States Patent
van Venrooij

(10) Patent No.: US 11,497,908 B2
(45) Date of Patent: Nov. 15, 2022

(54) SCREWLESS IMPLANTABLE MEDICAL LEAD EXTENSION

(71) Applicant: Medtronic Bakken Research Center B.V., Maastricht (NL)

(72) Inventor: Paulus C. van Venrooij, Hoensbroek (NL)

(73) Assignee: Medtronic Bakken Research Center, B.V., Maastricht (NL)

( * ) Notice: Subject to any disclaimer, the term of this patent is extended or adjusted under 35 U.S.C. 154(b) by 237 days.

(21) Appl. No.: 16/712,304

(22) Filed: Dec. 12, 2019

(65) Prior Publication Data
US 2021/0178150 A1 Jun. 17, 2021

(51) Int. Cl.
*A61N 1/05* (2006.01)
*A61N 1/375* (2006.01)

(52) U.S. Cl.
CPC ............ *A61N 1/05* (2013.01); *A61N 1/3752* (2013.01)

(58) Field of Classification Search
CPC ................................. A61N 1/05; A61N 1/3752
See application file for complete search history.

(56) References Cited

U.S. PATENT DOCUMENTS

| | | | |
|---|---|---|---|
| 2005/0222656 A1 | 10/2005 | Wahlstrand et al. | |
| 2006/0089681 A1* | 4/2006 | Tumlinson | A61N 1/3752 607/37 |
| 2013/0123866 A1* | 5/2013 | McDonald | A61N 1/3752 607/2 |
| 2015/0025609 A1 | 1/2015 | Govea | |
| 2015/0209575 A1 | 7/2015 | Black | |
| 2017/0143978 A1 | 5/2017 | Barker | |
| 2017/0361108 A1 | 12/2017 | Leven | |
| 2018/0008832 A1 | 1/2018 | Leven | |
| 2019/0083793 A1* | 3/2019 | Nageri | A61N 1/37241 |

OTHER PUBLICATIONS

International Search Report and Written Opinion of International Application No. PCT/EP2020/085355, dated Mar. 19, 2021, 14 pp.

* cited by examiner

*Primary Examiner* — Paula J Stice
(74) *Attorney, Agent, or Firm* — Shumaker & Sieffert, P.A.

(57) ABSTRACT

The disclosure describes a medical lead system that includes a first lead portion and a second lead portion. The first lead portion includes a first elongate body extending along a longitudinal axis from a distal end to a proximal end and defining a coupling recess. The second lead portion includes a second elongate body extending along the longitudinal axis from a distal end to a proximal end and a connector defining a channel configured to receive the proximal end of the first lead portion. The connector includes a coupling member configured to, when the first lead portion is inserted into the channel, mechanically engage the coupling recess to secure the first lead portion to the second lead portion at least in an axial direction relative to the longitudinal axis.

22 Claims, 13 Drawing Sheets

SCREWLESS IMPLANTABLE MEDICAL LEAD EXTENSION

TECHNICAL FIELD

This disclosure relates to medical device systems, and more specifically, connections between components of a medical device system.

BACKGROUND

Medical devices may be used to deliver therapy to a patient to treat symptoms or conditions such as chronic pain, seizure disorders (e.g., epilepsy), heart arrhythmias (e.g., fibrillation), tremor, Parkinson's disease, other types of movement disorders, obesity, mood disorders, urinary or fecal incontinence, or other types of symptoms or conditions. This therapy may be electrical stimulation therapy. Medical devices, such as implantable medical devices (IMDs), may be used for therapies such as deep brain stimulation (DBS), spinal cord stimulation (SCS), sacral neuromodulation (SNM), pelvic stimulation, gastric stimulation, peripheral nerve stimulation (PNS), cardiac stimulation, functional electrical stimulation, or other types of stimulation.

SUMMARY

The disclosure describes medical leads and lead systems for delivering a therapy to a patient. For example, a medical lead system may be configured to deliver electrical stimulation and/or sense electrical signals of a patient using a medical electrical lead ("lead") having one or more electrodes. The lead may be configured to be electrically coupled to electrical circuitry of an implantable medical device IMD via a medical lead extension ("lead extension"). Mechanically coupling the lead to the lead extension may subject the lead and/or the lead extension to stresses, such as torque, compression, or tension. For example, a mechanical coupling including one or more setscrews may induce a torque and/or a compression of components in the lead and/or lead extension due to tightening the one or more setscrews. Additionally, a fixed mechanical coupling, such as one or more setscrews, may prevent relief of stresses, such as compression, tension, or torsion, created by bends or twists in the lead and/or lead extension during an implant procedure.

The disclosure describes medical device systems that include a connector configured to mechanically couple a lead to a medical lead extension or a lead to an IMD. The connector may include a screwless and/or free-rotating mechanical coupling. The connector enables fixing the lead relative to the lead extension in an axial direction while, optionally, allowing rotation about a longitudinal axis of the lead and the lead extension in one or both directions.

In some examples, the disclosure describes a medical lead system that includes a first lead portion and a second lead portion. The first lead portion includes a first elongate body extending along a longitudinal axis from a distal end to a proximal end and defining a coupling recess. The second lead portion includes a second elongate body extending along the longitudinal axis from a distal end to a proximal end and a connector defining a channel configured to receive the proximal end of the first lead portion. The connector includes a coupling member configured to, when the first lead portion is inserted into the channel, mechanically engage the coupling recess to secure the first lead portion to the second lead portion at least in an axial direction relative to the longitudinal axis. One of the first lead portion or the second lead portion carries one or more electrodes.

In some examples, the disclosure describes a medical lead system that includes a first lead portion and a second lead portion. The first lead portion includes a first elongate body, extending along a longitudinal axis from a distal end to a proximal end, and coupling member. The second lead portion includes a second elongate body extending along the longitudinal axis from a distal end to a proximal end. The distal end of the second lead portion includes a connector defining a channel configured to receive the proximal end of the first lead portion. The connector also defines a coupling recess. The coupling member of the first lead portion is configured to, when the first lead portion is inserted into the channel of the second lead portion, mechanically engage the coupling recess of the connector to secure the first lead portion to the second lead portion at least in an axial direction relative to the longitudinal axis. One of the first lead portion or the second lead portion carries one or more electrodes.

In some examples, the disclosure describes a medical lead system that includes an elongate body extending along a longitudinal axis from a distal end to a proximal end. The elongate body defines a coupling recess. The proximal end of the elongate body is configured to be received in a channel defined by a connector extending from a distal end of a medical lead extension. The coupling recess, when the proximal end of the elongate body is inserted into the channel of the lead extension, is configured to receive a coupling member of the lead extension to mechanically secure the elongate body to the lead extension at least in an axial direction relative to the longitudinal axis.

In some examples, the disclosure describes a medical lead system that includes an elongate body extending along the longitudinal axis from a distal end to a proximal end and a connector extending from the distal end of the elongate body. The connector defines a channel configured to receive a proximal end of a medical lead. The connector comprises a coupling member configured to, when the proximal end of the lead is inserted into the channel, mechanically engage a coupling recess defined by the proximal end of the lead to secure the lead to the lead extension at least in an axial direction relative to the longitudinal axis.

The details of one or more aspects of the disclosure are set forth in the accompanying drawings and the description below. Other features, objects, and advantages will be apparent from the description and drawings, and from the claims.

DETAILED DESCRIPTION

Figure 1:
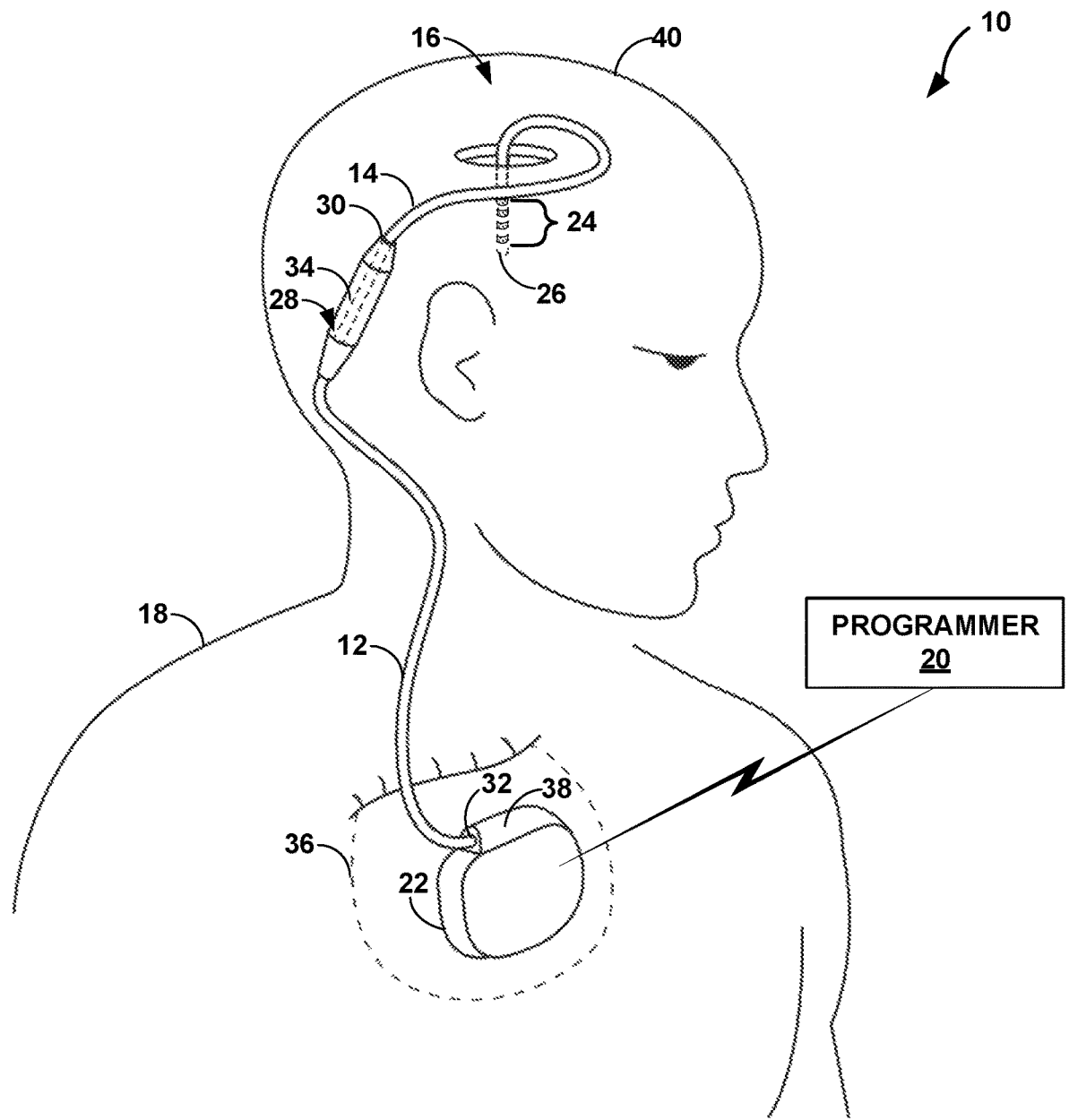
FIG. 1 is a conceptual diagram illustrating an example medical lead system including a lead extension and a lead implanted in the brain of a patient.

The disclosure relate to medical leads and medical lead systems ("lead systems") that include medical leads and medical lead extensions. A medical lead ("lead") may include one or more electrically conductive electrodes and/or one or more electrically conductive terminals ("electrical terminals") that are electrically coupled by one or more electrically conductive wires or other conductive material ("electrical conductors"). A medical lead extension ("lead extension") may include one or more connectors each having one or more electrically conductive contacts ("electrical contacts") that are configured to electrically couple, by one or more electrical conductors within the lead extension, the lead to an implantable medical device (IMD). Using the lead and the lead extension, the IMD may deliver or sense electrical signals to provide therapy to a patient to treat a patient condition. Electrical stimulation from a medical device electrically connected to the connector may be conducted along the conductors to be delivered across a surface of the electrode.

Typically, one or more setscrews are used to mechanically couple a lead to a lead extension. Tightening the setscrews, or bending or twisting the lead or lead extension during implant, may subject the lead and/or lead extension to torque, compression, or tension. In this way, components of the lead and/or components of the lead extension may experience compressive, tensile, or shear stresses. For example, a setscrew configured to mechanically engage an electrical terminal of the lead may result in a compressive force on the electrical terminal and/or electrical conductors of the lead. As another example, when a setscrew mounted to the connector of the lead extension is torqued to mechanically engage an electrical terminal of the lead, the torque may result in a torsion of the connector (e.g., the setscrew mount) and/or electrical conductors within the lead and/or lead extension. As another example, a fixed mechanical coupling, such as one or more setscrews, may prevent the lead from moving axially or rotating with respect to the lead extension which may cause bends or twists in the lead and/or lead extension and a torque, compression, or tension of the electrical conductors of the lead and/or the lead extension. In some examples, if the lead and/or the lead extension are exposed to a threshold torque or compression and/or a compression, tension, or torsion resulting from a bend and/or a twist, these forces may result in failure of components of the lead (e.g., the electrical conductors or the electrical terminals of the lead) and/or components of the lead extension (e.g., the electrical conductors, the electrical contacts, or the connector of the lead extension). Failure of one or more components of the lead or the lead extension may alter or prevent transmission of the electrical stimulation or other electrical signals from the IMD to the electrodes.

According to embodiments of the disclosure, a medical lead may include a connector configured to mechanically couple a lead to a medical lead extension. In other examples, the lead may couple directly to an implantable medical device. The connector may include a screwless and/or free-rotating mechanical coupling. The connector enables fixing the lead relative to the lead extension in an axial direction while, optionally, allowing rotation about a longitudinal axis of the lead and the lead extension in one or both directions. Because the connector is screwless, the connector does not require torsion or compression for mechanical coupling of the lead to the lead extension. Additionally, or alternatively, because the connector allows for rotation of the lead relative to the lead extension, the connector may enable relief of compression, tension, or torsion introduced in the lead or lead extension during implant. In this way, example leads systems discussed herein may reduce failure of the lead and/or the lead extension during an implant procedure, failure cause by stresses imparted on the lead and/or the lead extension during implanting, or both.

Implantable medical leads as discussed herein may be used in a variety of systems, including systems configured to provide therapy and/or sense physiological signals. FIG. 1 is a conceptual diagram illustrating an example medical lead system 10 including lead extension 12 and lead 14 implanted subcutaneously, where a distal portion of lead 14 is implanted within the brain 16 of patient 18. For ease of illustration, examples of the disclosure will primarily be described with regard to implantable electrical stimulation leads and implantable medical devices that apply neurostimulation therapy to brain 16 of patient 18 in the form of deep brain stimulation (DBS). However, the systems and techniques described herein may be useful in other types of medical device systems that employ medical leads to deliver electrical stimulation to a patient and/or sense electrical signals via one or more electrodes of the medical lead. For example, the systems and techniques described herein may be used in systems with medical devices that deliver stimulation therapy to a patient's heart, such as, for example, pacemakers, and pacemaker-cardioverter-defibrillators. As other examples, the systems and techniques described herein may be embodied in systems that deliver other types of neurostimulation therapy (e.g., spinal cord stimulation or vagal stimulation), stimulation of at least one muscle or muscle groups, stimulation of at least one organ such as gastric system stimulation, stimulation concomitant to gene therapy, and, in general, stimulation of any tissue of a patient. The medical lead system may be used with human subjects or with non-human subjects.

As illustrated in FIG. 1, medical lead system 10 includes external medical device programmer 20, implantable medical device (IMD) 22, lead extension 12, and lead 14. Lead 14 includes plurality of electrodes 24 adjacent a distal end 26 of lead 14. IMD 22 includes switching circuitry that includes an electrical stimulation generator that generates and delivers electrical stimulation therapy to one or more regions of brain 16 of patient 18 via one or more of electrodes 24. In the example illustrated in FIG. 1, medical lead system 10 may be referred to as a DBS system because IMD 22 provides electrical stimulation therapy directly to tissue within brain 16, e.g., a tissue site under the dura mater of brain 16. In other examples, lead 14 may be positioned to deliver therapy to a surface of brain 16 (e.g., the cortical surface of brain 16), or to cranial nerves of brain 16 or peripheral nerves on the head.

Lead 14 extends from distal end 26 to proximal end 28. Lead extension 12 extends from a distal end 30 to a proximal end 32. A proximal portion of lead 14, e.g., near proximal end 28, and a distal portion of lead extension 12, e.g., near distal end 30, are electrically and mechanically coupled at connector 34. Connector 34 is configured to electrically and mechanically couple the proximal portion of lead 14 to the distal portion of lead extension 12 without torsion or compression. In some examples, connector 34 may extend from or be integrally formed with the distal portion of lead extension 12. In other examples, connector 34 may extend from or be integrally formed with the proximal portion of lead 14. Additionally, or alternatively, connector 34 allows rotation of lead 14 relative to lead extension 12. Rotation may include rotation greater than a threshold degree, such as more than 90 degrees, more than 180 degrees, or more than 360 degrees.

Lead extension 12 and lead 14 may be constructed of any suitable materials or combination of materials. Lead extension 12 and/or lead 14 may include one or more electrical conductors, such as, for example, one or more wires, filaments, braids, or other elongate electrically conductive members. The elongate electrically conductive members may include one or more conductive materials, such as, for example, platinum, palladium, iridium, titanium and titanium alloys such as titanium molybdenum alloy (TiMoly), nickel and nickel alloys such as MP35N alloy, and the like. Lead extension 12 and/or lead 14 may include at respective proximal ends and distal ends, respective electrical terminals or electrical contacts that are coupled to respective electrical conductors. The electrical terminals or electrical contacts may include any one or more of the above conductive materials. Lead extension 12 and/or lead 14 may include an electrically insulative material surrounding the one or more elongate electrically conductive members. The insulative material may include, for example, polymeric materials, polyurethanes, silicones, fluoropolymers, fluoroelastomers, polyethylenes, polyesters, epoxies, or biocompatible polymers suitable for contact with bodily tissue. In some examples, lead extension 12 and/or lead 14 also may include an outer jacket surrounding the insulative material. The outer jacket may include, for example, polyurethane, silicone, silicon-polyurethane blends, or biocompatible polymers suitable for contact with bodily tissue.

In some examples, medical lead system 10 may include an electrical connection sleeve block 38 adjacent proximal end 32 of lead extension 12 that is configured to electrically and mechanically couple lead extension 12 to IMD 22. In this way, using the conductive pathways of lead extension 12 and lead 14, IMD 22 may deliver electrical stimulation to brain 16 of patient 18 and/or sense electric signals of brain 16 using electrodes 24. Although described as including lead extension 12, in some example, lead 14 may be directly connected to IMD 22 that includes a connector 34, such as any of the connector described herein.

In the example illustrated in FIG. 1, IMD 22 may be implanted within a subcutaneous pocket 36 below the clavicle of patient 18. In other examples, IMD 22 may be implanted within other regions of patient 18, such as a subcutaneous pocket 36 in the abdomen or buttocks of patient 18 or proximate the cranium 40 of patient 18, e.g., between the scalp and the skull. Connection sleeve block 38, which couples proximal end 32 of lead extension 12 to IMD 22, may include, for example, electrical contacts that electrically couple to respective electrical contacts at proximal end 32 of lead extension 12. The electrical contacts electrically couple the electrodes 24 carried by distal end 26 of lead 14 to IMD 22 through conductors (not illustrated). Lead extension 12 and lead 14 traverse from the implant site of IMD 22 within a chest cavity of patient 18, along the neck of patient 18 and through cranium 40 of patient 18 to access brain 16. Generally, IMD 22 is constructed of a biocompatible material that resists corrosion and degradation from bodily fluids. IMD 22 may comprise a hermetic housing to substantially enclose components, such as processing circuitry, therapy circuitry, and memory. Although illustrated as an implantable device, in other examples, IMD 22 may include a non-implantable medical device.

Lead 14 may be positioned to deliver electrical stimulation to one or more target tissue sites within brain 16 to manage patient symptoms associated with a disorder of patient 18. Lead 14 may be implanted to position electrodes 24 at desired locations of brain 16 through respective holes in cranium 40. Lead 14 may be placed at any location within brain 16 such that electrodes 24 are capable of providing electrical stimulation to target tissue sites within brain 16 during treatment. Although FIG. 1 illustrates system 10 as including a single lead 14 coupled to IMD 22, in some examples, system 10 may include more than one lead.

Lead 14 may deliver electrical stimulation via electrodes 24 to treat any number of neurological disorders or diseases in addition to movement disorders, such as seizure disorders or psychiatric disorders. Lead 14 may be implanted within a desired location of brain 16 via any suitable technique, such as through respective burr holes in a skull of patient 18, through a common burr hole in cranium 40, or through a craniotomy. Lead 14 may be placed at any location within brain 16 such that electrodes 24 of lead 14 are capable of providing electrical stimulation to targeted tissue during treatment. In the examples illustrated in FIG. 1, electrodes 24 of lead 14 are illustrated as segmented electrodes and ring electrodes. Electrodes 24 of lead 14 may have a complex electrode array geometry that is capable of producing shaped electrical fields. In this manner, electrical stimulation may be directed to a specific direction from lead 14 to enhance therapy efficacy and reduce possible adverse side effects from stimulating a large volume of tissue.

IMD 22 may deliver electrical stimulation therapy to brain 16 of patient 18 according to one or more stimulation therapy programs. A therapy program may define one or more electrical stimulation parameter values for therapy generated and delivered from IMD 22 to brain 16 of patient 18. Where IMD 22 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities. The exact therapy parameter values of the stimulation therapy that helps manage or treat a patient disorder may be specific for the particular target stimulation site (e.g., the region of the brain) involved as well as the particular patient and patient condition.

In addition to delivering therapy to manage a disorder of patient 18, medical lead system 10 monitors electrical signals, such as, e.g., one or more bioelectrical brain signals of patient 18. For example, IMD 22 may include sensing circuitry that senses bioelectrical brain signals within one or more regions of brain 16. In the example illustrated in FIG. 1, the signals generated by electrodes 24 are conducted to the sensing circuitry within IMD 22 via conductors within lead 14 and lead extension 12, including one or more conductors within lead 14 and lead extension 12 between distal end 26 of lead 14 and proximal end 32 of lead extension 12.

Programmer 20 may wirelessly communicate with IMD 22 to provide or retrieve therapy information. In some examples, programmer 20 may be directly coupled to IMD 22 via one or more wired connections. Programmer 20 is an external computing device that the user, e.g., the clinician and/or patient 18, may use to communicate with IMD 22. For example, programmer 20 may be a clinician programmer that the clinician uses to communicate with IMD 22 and program one or more therapy programs for IMD 22. Alternatively, programmer 20 may be a patient programmer that allows patient 18 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 22.

Programmer 20 may be a hand-held computing device with a display viewable by the user and an interface for providing input to programmer 20 (i.e., a user input mechanism). In other examples, programmer 20 may be a larger workstation or a separate application within another multi-function device, rather than a dedicated computing device. For example, the multi-function device may be a notebook computer, tablet computer, workstation, cellular phone, personal digital assistant, or another computing device that may run an application that enables the computing device to operate as a secure medical device programmer 20.

While lead 14 and lead extension 12 are described herein for use in DBS applications, lead 14 or other leads (such as lead extension 12) may be configured to be implanted at any other location within patient 18. For example, lead 14 may be implanted near the spinal cord, pudendal nerve, sacral nerve, or any other nervous or muscle tissue that may be stimulated. The user interface described herein may be used to program the stimulation parameters of any type of stimulation therapy. In the case of pelvic nerves, defining a stimulation field may allow the clinician to stimulate multiple desired nerves without placing multiple leads deep into patient 18 and adjacent to sensitive nerve tissue. Therapy may also be changed if lead 14 migrates to new locations within the tissue or patient 18 no longer perceives therapeutic effects of the stimulation. The features or techniques of this disclosure may be useful in other types of medical applications.

Figure 2:
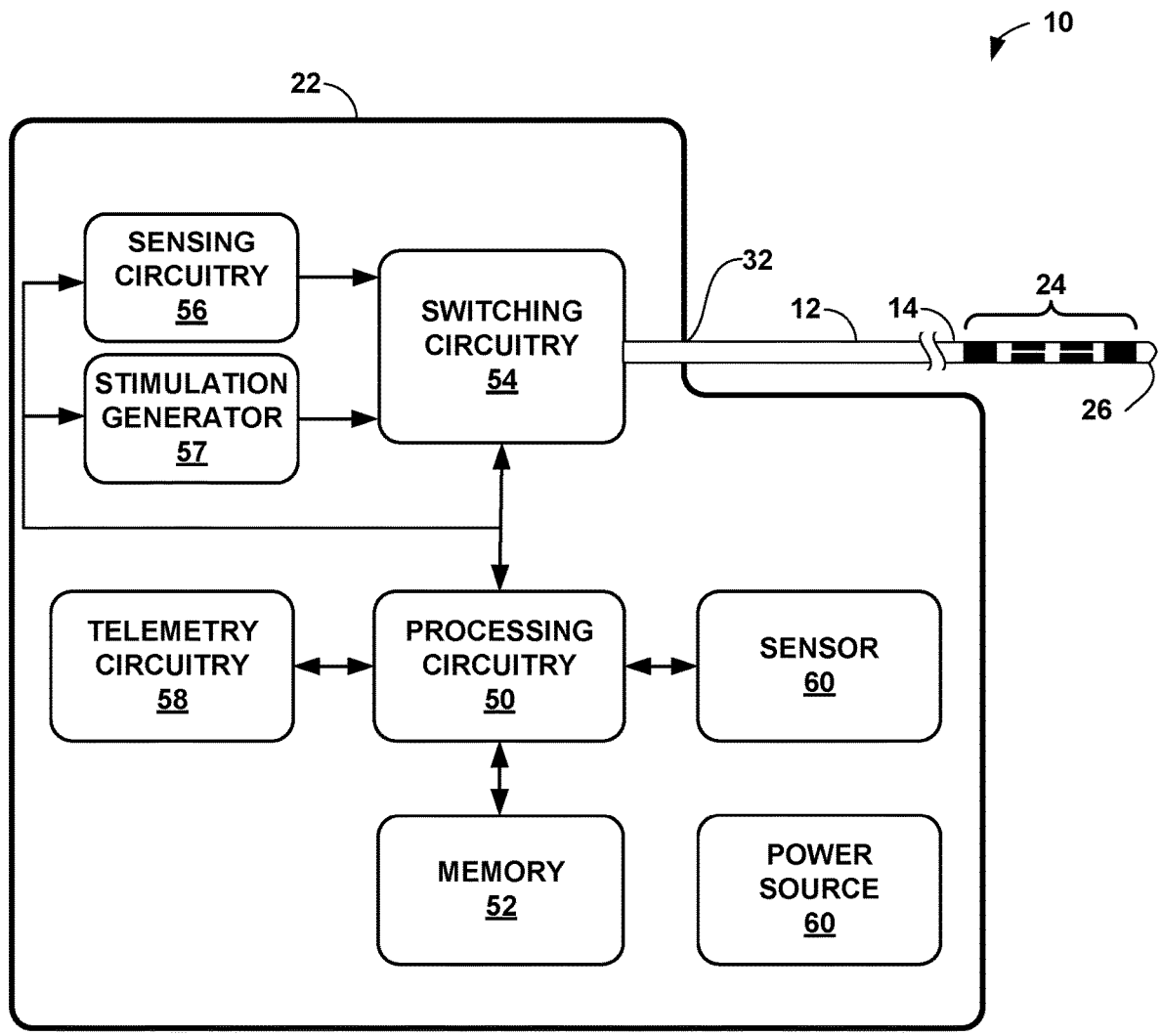
FIG. 2 is a functional block diagram illustrating components of the IMD illustrated in FIG. 1.

FIG. 2 is a functional block diagram illustrating components of IMD 22. As illustrated, medical lead system 10 includes IMD 22 coupled to lead 14 through lead extension 12. In some examples, IMD 22 may be configured to couple to more than one lead and/or lead extension, such as two or more leads and/or lead extensions. In the example of FIG. 2, IMD 22 includes processing circuitry 50, memory 52, switch circuitry 54, sensing circuitry 56, telemetry circuitry 58, sensor 60, and power source 62. Processing circuitry 50 may include any one or more microprocessors, controllers, digital signal processors (DSPs), application specific integrated circuits (ASICs), field-programmable gate arrays (FPGAs), or discrete logic circuitry. The functions attributed to processors described herein, including processing circuitry 50, may be provided by processing circuitry of a hardware device, e.g., as supported by software and/or firmware. Processing circuitry 50 controls switch circuitry to apply particular stimulation parameter values, such as amplitude, pulse width, and pulse rate.

Memory 52 may include any volatile or non-volatile media, such as a random-access memory (RAM), read only memory (ROM), non-volatile RAM (NVRAM), electrically erasable programmable ROM (EEPROM), flash memory, and the like. Memory 52 may store computer-readable instructions that, when executed by processing circuitry 50, cause IMD 22 to perform various functions. Memory 52 may be a storage device or other non-transitory medium.

In the example illustrated in FIG. 2, lead 14 includes electrodes 24 located at distal end 26. Processing circuitry 50 also controls switch circuitry 54 to generate and apply the stimulation signals. In some examples, the stimulation signals may be generated by a stimulation generator 57. In some examples, the stimulation signals may be supplied to selected combinations of electrodes. In some examples, switch circuitry 54 couples stimulation signals to selected conductors within lead 14 and lead extension 12, which, in turn, delivers the stimulation signals across selected electrodes. Such switching circuitry 54 may be a switch array, switch matrix, multiplexer, or any other type of switching circuitry configured to selectively couple stimulation energy to selected electrodes and to selectively sense bioelectrical neural signals of the spine with selected electrodes.

In some examples, stimulation generator 57 includes a plurality of pairs of voltage sources, current sources, voltage sinks, or current sinks connected to each of electrodes such that each pair of electrodes has a unique signal generator. In other words, in these examples, each of electrodes is independently controlled via its own stimulation generator 57 (e.g., via a combination of a regulated voltage source and sink or regulated current source and sink), as opposed to switching signals between electrodes.

Switching circuitry 54 may be a single channel or multi-channel stimulation generator. In particular, switching circuitry 54 may be capable of delivering a single stimulation pulse or multiple stimulation pulses at a given time via a single electrode combination or multiple stimulation pulses at a given time via multiple electrode combinations. In some examples, however, switching circuitry 54 may be configured to deliver multiple channels on a time-interleaved basis. For example, switching circuitry 54 may serve to time divide the output of switching circuitry 54 across different electrode combinations at different times to deliver multiple programs or channels of stimulation energy to patient 18. In another example, the switching circuitry 54 may control the independent sources or sinks on a time-interleaved bases.

Lead extension 12 may include distal end 26 including a complex electrode array geometry, but may also include one or more single ring electrodes along the longitudinal axis in other examples. In one example, distal end 26 of lead 14 includes a plurality of electrodes 24 positioned at different axial positions along the longitudinal axis of the lead and a plurality of electrodes 24 positioned at different angular positions around the circumference of the lead (which may be referred to as electrode segments). In this manner, electrodes may be selected along the longitudinal axis of lead 14 and along the circumference of the lead. Selectively activating electrodes 24 of lead 14 can produce customizable stimulation fields that may be directed to a particular side of lead 14 in order to isolate the stimulation field around the target anatomical region of brain 16. These techniques may also be applied to leads having more or fewer than two ring electrodes. In yet other cases, lead 14 may include only segmented electrodes or only ring electrodes.

Although sensing circuitry 56 is incorporated into a common housing with stimulation generator 57 and processing circuitry 50 in FIG. 2, in other examples, sensing circuitry 56 may be in a separate housing from IMD 22 and may communicate with processing circuitry 50 via wired or wireless communication techniques. Example bioelectrical signals include, but are not limited to, a signal generated from local field potentials within one or more regions of the spine or brain, for example.

Sensor 60 may include one or more sensing elements that sense values of a respective patient parameter. For example, sensor 60 may include one or more accelerometers, optical sensors, chemical sensors, temperature sensors, pressure sensors, or any other sensor configured to sense a patient parameter. Sensor 60 may output patient parameter values that may be used as feedback to control delivery of therapy. IMD 22 may include additional sensors within the housing of IMD 22 and/or coupled as a separate module via one of lead 50 or other leads. In addition, IMD 22 may receive sensor signals wirelessly from one or more remote sensors via telemetry circuitry 58, for example. In some examples, the one or more remote sensors may be external to patient (e.g., carried on the external surface of the skin, attached to clothing, or otherwise positioned external to the patient).

Telemetry circuitry 58 supports wireless communication between IMD 22 and an external programmer (e.g., such as programmer 20) or another computing device under the control of processing circuitry 50. Processing circuitry 50 of IMD 22 may receive, as updates to programs, values for various stimulation parameters such as amplitude and electrode combination, from programmer 20 via telemetry circuitry 58. Telemetry circuitry 58 in IMD 22, as well as telemetry circuitry in other devices and systems described herein, such as programmer 20, may accomplish communication by radiofrequency (RF) communication techniques. Addition, or alternatively, telemetry circuitry 58 may communicate with external medical device programmer 20 via proximal inductive interaction of IMD 22 with programmer 20. Accordingly, telemetry circuitry 58 may send information to programmer 20 on a continuous basis, at periodic intervals, or upon request from IMD 22 or programmer 20.

Power source 62 delivers operating power to various components of IMD 22. Power source 62 may include a rechargeable or non-rechargeable battery and a power generation circuit to produce operating power. Recharging may be accomplished through proximal inductive interaction between an external charger and an inductive charging coil within IMD 22. In some examples, power requirements may be small enough to allow IMD 22 to utilize patient motion and implement a kinetic energy-scavenging device to trickle charge a rechargeable battery. In other examples, traditional batteries may be used for a limited period of time.

Figure 3A:
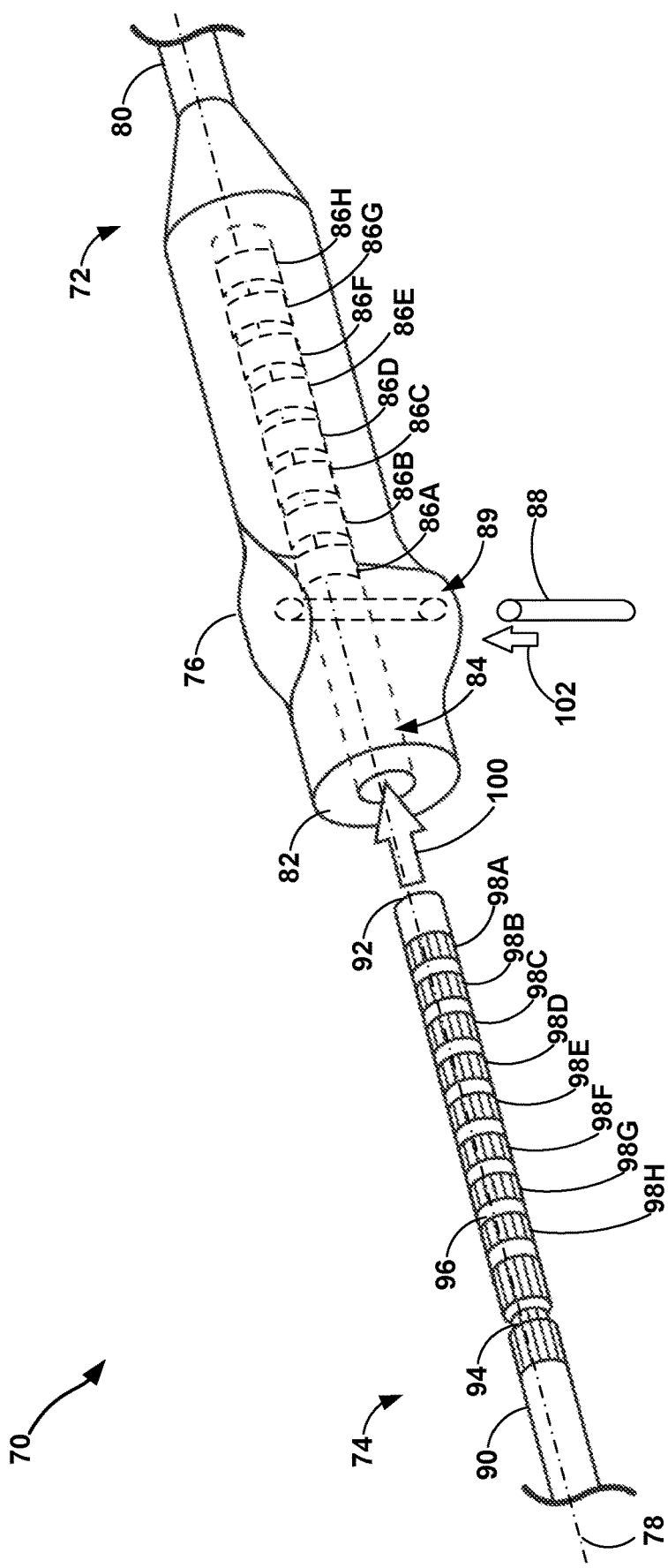
FIG. 3A is a conceptual diagram illustrating a perspective view of an example connector of a medical lead system.

As explained above, the medical leads and lead systems disclosed herein may include connectors fixing the lead relative to the lead extension in an axial direction without setscrews and, optionally, allow rotation of the lead is the circumferential direction relative to the lead extension. FIG. 3A is a conceptual diagram illustrating a perspective view of an example connector 76 of a medical lead system 70. Medical lead system 70 may be the same as or substantially similar to medical lead system 10 discussed above in reference to FIGS. 1 and 2, except for the differences described herein. For example, lead extension 72 and lead 74 may include examples of lead extension 12 and lead 14, respectively.

Medical lead system 70 include lead extension 72 and lead 74. Lead extension 72 includes elongate body 80 and connector 76. Elongate body 80 extends along a longitudinal axis 78 from a distal end 82 to a proximal end (not shown). Connector 76 defines a channel 84 that is configured to receive proximal end 92 of lead 74. For example, proximal end 92 of lead 74 may define a male connector that may be inserted into channel 84 of corresponding female connector 76.

Connector 76 includes a coupling member 88. Coupling member 88 is configured to, when proximal end 92 of lead 74 is inserted into channel 84, mechanically engage a corresponding coupling member (e.g., coupling recess 94, described below) of lead 74 to secure lead extension 72 to lead 74 at least in the axial direction relative to longitudinal axis 78. Although illustrated as a discrete component, in some example, coupling member 88 may be affixed or integrally formed with connector 76. Coupling member 88 may include any suitable mechanical coupling. As illustrated in FIG. 3, coupling member 88 includes a pin configured to be received in an aperture 89 defined by connector 76. In examples in which the corresponding coupling member of lead 74 includes a recess, aperture, or other feature extending radially inward, coupling member 88 may include, for example, a displaceable protrusion, such as a movable post, bar, or hook; a spring-loaded push button; a resilient lever, spring, or clip; or other reversible or non-reversible (e.g., relative to disengaged and engaged configurations) mechanical coupling having a feature configured to engage the corresponding coupling member of lead 74. In examples, in which the corresponding coupling member of lead 74 includes displaceable protrusion or the like, coupling member 88 may include, for example, a recess, aperture, or other feature extending radially outward (e.g., relative to channel 84).

Connector 76 may include any suitable dimensions. In some examples, a length of connector may be within a range from about 7 mm to about 60 mm, such as from about 32 mm to about 52 mm. Although connector 76 is illustrated as having a greater diameter than elongate body 80, in some examples, elongate body 80 and connector 76 may have the same diameter or a similar diameter. In some examples, a diameter of connector 76 may be selected based on a diameter of a tunneling tool configured to implant lead extension 72 into a body of a patient.

The radially inward facing surface of connector 76 that defines channel 84 includes a plurality of electrical contacts 86A-86H (collectively, "electrical contacts 86"). In some examples, connector 76 may include a different number of electrical contacts 86, such as seven or fewer electrical contacts, or nine or more electrical contacts. In some examples, the number of electrical contacts may be limited by a selected diameter of connector 76 and a selected yield strength of the electrical contacts 86. Each electrical contact of electrical contacts 86 may be electrically coupled to a respective electrical conductor of a plurality of electrical conductors (not shown) of lead extension 72. A variety of methods may be used to electrically couple electrical contacts 86 to the electrical conductors including, but not limited to, laser welding, crimping, resistance welding, swaging, and the like. The electrical conductors may be electrically isolated from other electrical conductors in separate channels defined by elongate body 80, an electrically insulating sheath or coating, or the like. Additionally, each respective electrical conductor of a plurality of electrical conductors may be electrically coupled to one or more respective electrical contacts of an IMD (e.g., IMD 22 illustrated in reference to FIG. 1, such as switching circuitry 54 illustrated in reference to FIG. 2).

Lead 74 includes an elongate body 90 extending along longitudinal axis 78 from a distal end (not shown) to a proximal end 92. Lead 74 includes a coupling member configured to engage (or be engaged by) a corresponding coupling member of lead extension 72. As illustrated in FIG. 3, the coupling member includes a coupling recess 94. For example, elongate body 90 may define a major surface 96. A radially inward displacement of major surface 96, e.g., a different surface that has a radius smaller than the radius of major surface 96, defines coupling recess 94. Coupling recess 94 may extending around at least a portion of a circumference of elongate body 90. For example, coupling recess 94 may extend about more than about 25%, such as more than about 50% or about 75%, of the circumference of elongate body 90. In some examples, coupling recess 94 may extend around the entire circumference of elongate body 90. In some examples, recess 94 be include an electrical contact, e.g., similar to electrical contacts 86A-86H.

Although illustrated as a recess, in other examples, the coupling member of lead 74 may include other features configured to engage (or be engaged by) a corresponding coupling member of lead extension 72. For example, the coupling member of lead 74 may include an aperture extending through a portion of elongate body 90 at any suitable angle, a displaceable protrusion, such as a movable post, bar, or hook; a spring-loaded push button; a resilient lever or clip; or other reversible or non-reversible mechanical coupling.

Lead 74 also includes a plurality of electrical terminals 98A-98H (collectively, "electrical terminals 98"). In some examples, lead 74 may include a different number of electrical terminals 98, such as seven or fewer electrical terminals, or nine or more electrical terminals. In some examples, the number of electrical terminals may be limited by a selected diameter of lead 74 and a selected yield strength of the electrical terminals. Each electrical terminal of electrical terminals 98 may be electrically coupled to a respective electrical conductor of a plurality of electrical conductors (not shown) of lead 74. A variety of methods may be used to electrically couple electrical terminals 98 to the electrical conductors including, but not limited to, laser welding, crimping, resistance welding, swaging, and the like. The electrical conductors may be electrically isolated from other electrical conductors in separate channels defined by elongate body 90, an electrically insulating sheath or coating, or the like. Additionally, each respective electrical conductor of a plurality of electrical conductors may be electrically coupled to one or more respective electrodes positioned at a distal end of lead 74 (e.g., electrodes 24 illustrated in reference to FIG. 1).

When proximal end 92 of lead 74 is inserted into channel 84 of connector 76, e.g., as indicated by arrow 100, each respective electrical contact of electrical contacts 86 may align with and physically contact a respective electrical terminal of electrical terminals 98. In this way, lead extension 72 is configured to electrically couple to lead 74. In some examples, lead 74 may include a ridge extending radially outward relative to major surface 96. When lead 74 is fully inserted into channel 84, the ridge may contact distal end 82 of lead extension to prevent lead 74 from extending beyond a selected distance into connector 76. In other examples, proximal end 92 may contact a proximal surface that defines channel 84 to stop electrical contacts 86 in alignment with respective electrical terminals 98. After inserting proximal end 92 of lead 74 into channel 84 of connector 76, coupling member 88 may be inserted into aperture 89, e.g., as indicated by arrow 102, to secure lead extension 72 to lead 74 at least in the axial direction relative to longitudinal axis 78 (e.g., without aid of any setscrews) and with substantially rotation of lead 74 relative to lead extension 72.

Figure 3B:
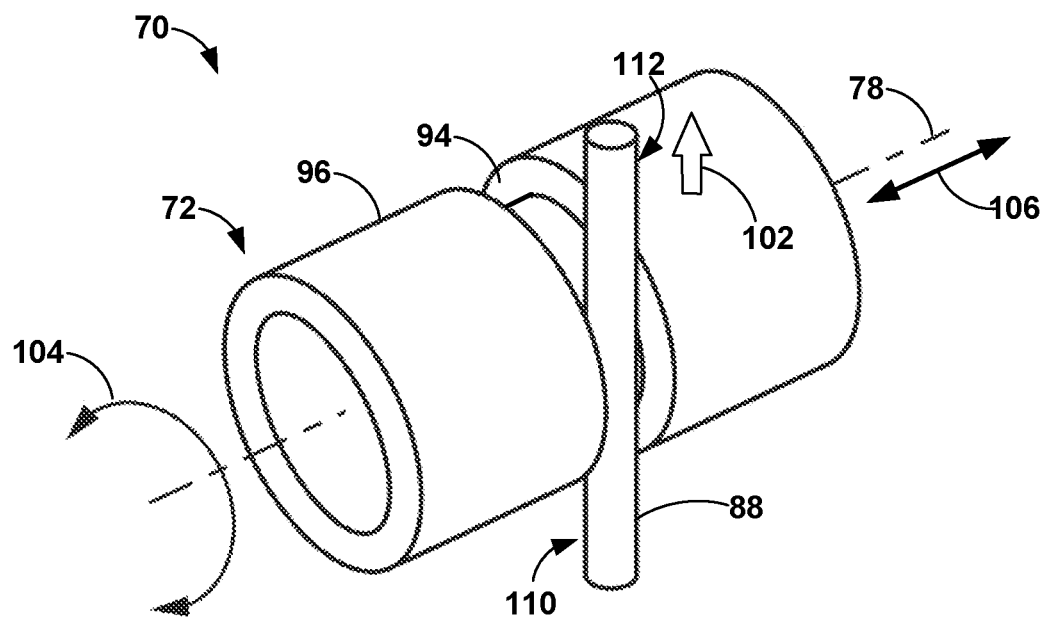
FIGS. 3B and 3C are a perspective view and a plan view illustrating the mechanical engagement of the coupling member with the coupling recess illustrated in FIG. 3A.
Figure 3C:
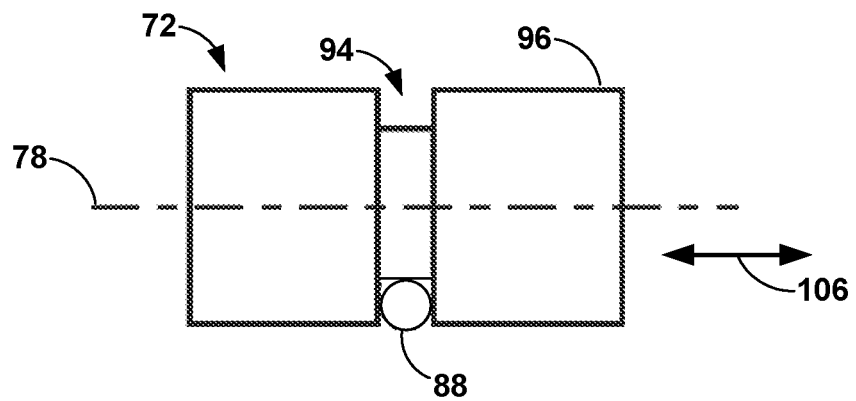

FIGS. 3B and 3C include a perspective view and a plan view illustrating the mechanical engagement of coupling member 88 with coupling recess 94. For purposes of illustration, connector 76 is not shown in FIGS. 3B and 3C. Coupling member 88 includes a cylindrical pin configured to friction fit within aperture 89. In one example, the pin may be substantially cylindrical, but may also taper from a proximal portion 110 to a distal portion 112. Connector 76 may define a corresponding taper defining aperture 89. When the tapered cylindrical coupling member 88 (e.g., a conical shape) is fully inserted into tapered aperture 89, coupling member 88 and the portion of connector 76 defining aperture may engage in a friction fit. In other examples, coupling member 88 may define other shapes, such as, polygonal prisms, keyed shaped, or the like. In some examples, coupling member may include a mechanical fastener configured to engage at least a portion of connector 76. For example, coupling member 88 may include a bolt configured to screw into threads formed in the portion of connector 76 that define aperture 89. As another example, coupling member 88 may include a mechanical fastener clip, such as a cotter pin, a spring clip, or the like.

When inserted into aperture 89, coupling member 88 prevents or at least impedes movement of lead 74 in the axial direction, e.g., the direction indicated by arrow 106, relative to lead extension 72, e.g., relative to connector 76 and/or coupling member 88. In this way, connector 76, e.g., coupling member 88, of lead extension 72 together with a corresponding coupling member of lead 74, e.g., coupling recess 94, fix lead 74 relative to lead extension 72 in the axial direction. By eliminating direct mechanical coupling from connector 76 to lead 74, e.g., using one or more setscrews, connector 76 may reduce compression or torqueing of lead extension 72, lead 74, and/or components thereof.

As illustrated in FIG. 3C, when coupling member 88 is inserted into aperture 89, coupling member 88 may enable partial or full rotation of lead 74 relative to lead extension 72, e.g., relative to connector 76 and/or coupling member 88. For example, as indicated by arrow 104, lead 74 may be free to rotate about longitudinal axis 78. As discussed above, coupling recess 94 may extend fully around a circumference of lead 74, thereby enabling rotation of 360-degrees. In some examples, coupling recess 94 may extend around less than the full circumference of lead 74, thereby limiting rotation to less than 360-degrees. By allowing rotation, connector 76 may be configured to relieve stresses in lead extension 72 and/or lead 74 that are caused by bending or twisting of lead extension 72 and/or lead 74 during an implant procedure.

In other examples, when coupling member 88 is inserted into aperture 89, coupling member 88 may interfere, e.g., by friction, with coupling recess 94 to at least partially interfere with the rotation of lead 74 relative to lead extension 72. By at least partially interfering with the rotation of lead 74 relative to lead extension 72, coupling member 88 may be configured to still relieve stresses caused by bending or twisting of lead extension 72 and/or lead 74 during an implant procedure, but also reduce excessive twisting or bending of the lead extension 72 and/or lead 74 caused by external pressure, such as a patient pressing on lead extension 72 and/or lead 74. In some examples, excessive twisting or bending may be transferred to the distal end of lead 74 (e.g., distal end 26) and disturb the orientation or position of the electrodes (e.g., electrodes 24). The coupling mechanism described herein, such as using coupling member 88 with coupling recess 94, may reduce or eliminate these twisting or rotational forces being transmitted between the lead and lead extension.

Figure 4A:
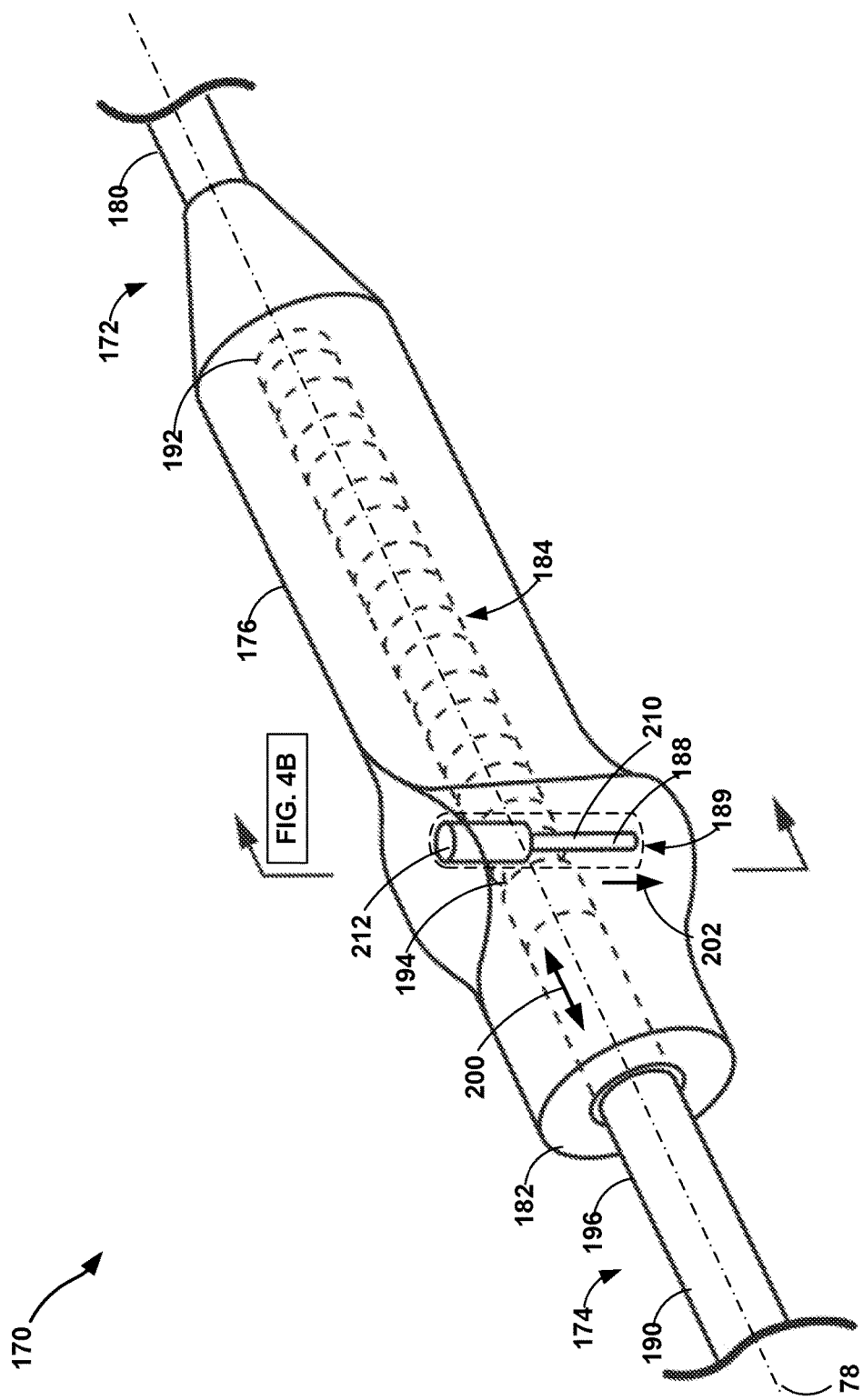
FIG. 4A is a conceptual diagram illustrating a perspective view of an example connector of a medical lead system.
Figure 4B:
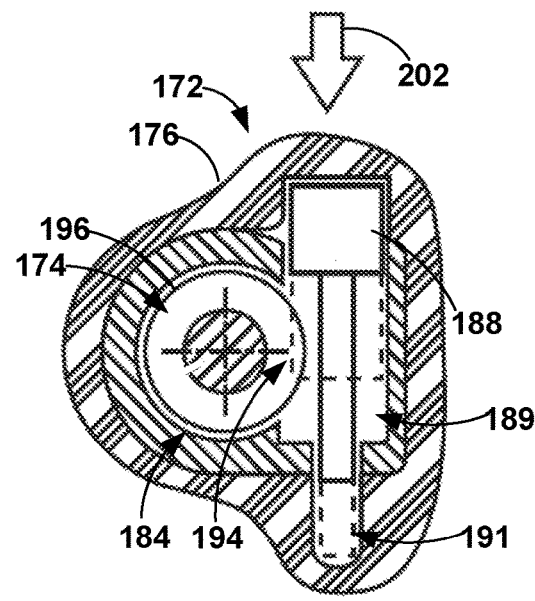
FIGS. 4B-4D are lateral cross sectional views of the connector, the lead and the coupling member in the disengaged configuration (FIGS. 4B and 4C), and the lead and the coupling member in the engaged configuration (FIG. 4D).
Figure 4C:
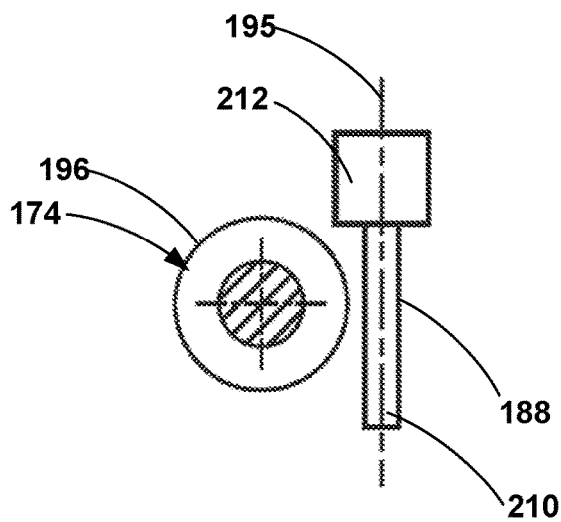
Figure 4D:
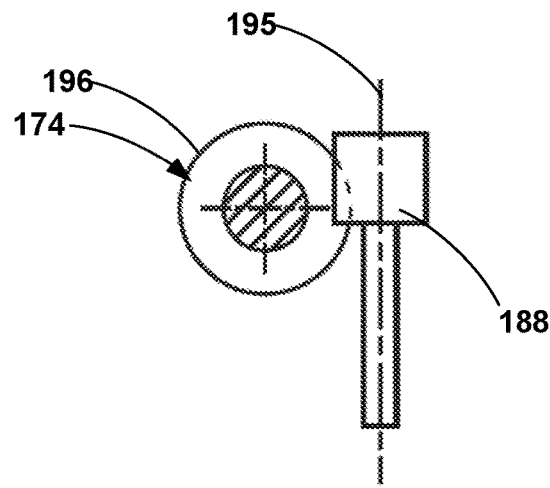

In some examples, coupling member 88 may include features configured to improve fitting within aperture 89. FIG. 4A is a conceptual diagram illustrating a perspective view of an example connector 176 of a medical lead system 170. FIG. 4B is a lateral cross sectional view of connector 176, and FIGS. 4C and 4D are lateral cross sectional views of lead 174 and coupling member 188 in the disengaged and engaged configurations, respectively. Medical lead system 170 may be the same as or substantially similar to medical lead system 10 and medical lead system 70 discussed above in reference to FIGS. 1-3C, except for the differences described herein.

Medical lead system 170 includes lead extension 172 and lead 174. Lead extension 172 includes an elongate body 180 extending from distal end 182 to a proximal end (not shown). Lead extension include connector 176 that defines a channel 184 configured to receive a proximal portion of lead 174. Lead 174 includes an elongate body 190 extending from a distal end (not shown) to proximal end 192. Elongate body 190 has a major surface 196 that defines coupling recess 194 that is configured to be engaged by coupling member 188 of connector 176.

As illustrated in FIG. 4B-4D, after inserting proximal end 192 of lead 174 into channel 184 of connector 176, a clinician may manipulate coupling member 188 to move coupling member 188 from a disengaged configuration (FIG. 4C, solid lines illustrating coupling member 188 in FIG. 4B), in the direction indicated by arrow 202, to an engaged configuration (FIG. 4D). Alternatively, the clinician may manipulate coupling member 188 to move coupling member 188 from an engaged configuration (FIG. 4D, dashed lines illustrating coupling member 188 in FIG. 4B), in the direction indicated by arrow 203, to a disengaged configuration (FIG. 4C).

As illustrated in FIGS. 4A and 4B, coupling member 188 is completely contained within connector 176. For example, coupling member 188 is disposed within channel 189 defined by connector 176. To enable manipulation, connector 176 may include a material configured to, for example, deflect in response to pressure applied by a finger of the clinician or a tool used by the clinician to enable the clinician to move coupling member 188. For example, the material of connector 176 may include those discussed above, such as, silicon. In some examples, connector 176 may include an elastic material configured to bias coupling member 188 toward the engaged configuration, e.g., in the direction of arrow 202. By enclosing coupling member 188, connector 176 may asepsis of medical lead system 170 and/or enable internal components of lead extension 172, lead 174, and/or connector 176, such as coupling member 188, to be formed from materials that may not be considered biocompatible.

Coupling member 188 includes a head portion 212 and a pin portion 210 extending from head portion 212. Head portion 212 may include any suitable shape, such as a cylinder, a sphere, a cube, or the like. Pin portion 210 may include any suitable shape, such as a pre-shaped pin defining head portion 212 as one or more arms of the pre-shaped pin. Pin portion 210 traverses channel 184 and 189, e.g., into pin receiving cavity 191. By traversing channel 184, pin portion 210 is configured to maintain a selected orientation of coupling member 188 when in the disengaged configuration. For example, pin portion 210 may keep coupling member 188 aligned with axis 195. Pin portion 210 has first diameter that is selected to not interfere with lead 174 when lead 174 is inserted into or withdrawn from channel 184. For example, as illustrated in FIGS. 4A-4C, when coupling member 188 is in the disengaged configuration, only pin portion 210 is positioned in channel 189 adjacent to coupling recess 194 such that lead 174 may travel in the axial direction within channel 184 of lead extension 172.

Head portion 212 has second diameter (larger than the first diameter) that is selected to engage coupling recess 194 of lead 174. In the disengaged configuration, head portion 212 extends into a head receiving cavity 193. When moved into the engaged configuration, head portion 212 is configured to engage coupling recess 194 of lead 174. For example, as illustrated in FIG. 4D, when head portion 212 is positioned in channel 189 adjacent coupling recess 194 such that lead 174 is secured in the axial direction.

Figure 5C:
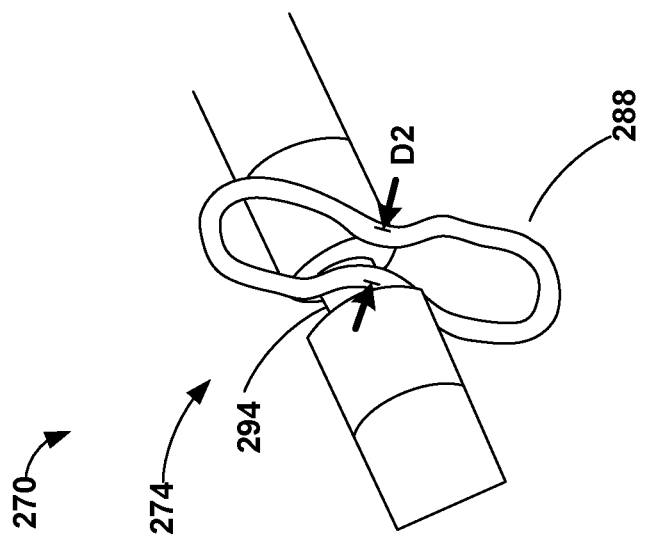
FIGS. 5A-5C are conceptual diagrams illustrating a perspective view of an example resilient band coupling member of a medical lead system.
Figure 5B:
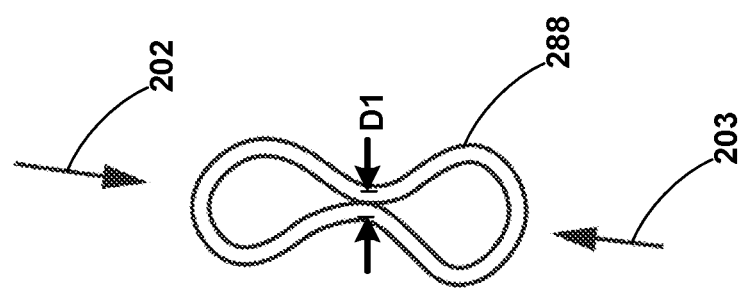
Figure 5A:
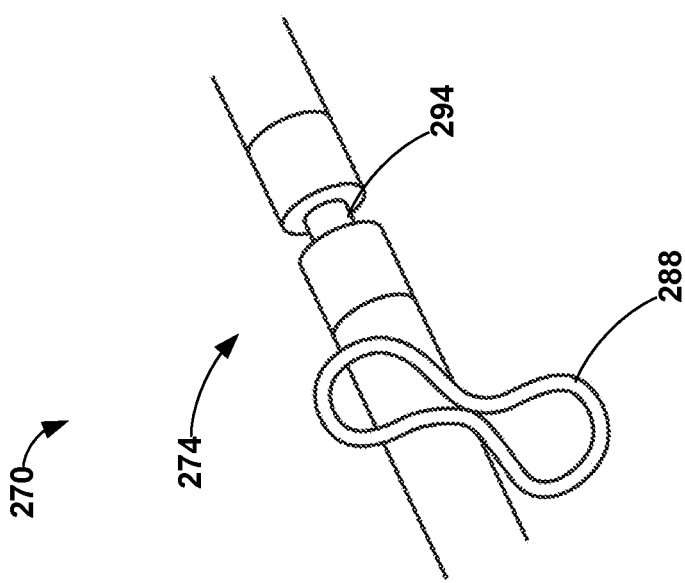

In some examples, rather than a pin, a coupling member may include a resilient band or a clip. FIGS. 5A-5C are conceptual diagrams illustrating a perspective view of an example resilient band coupling member 288 of a medical lead system 270. Medical lead system 270 may be the same as or substantially similar to medical lead systems 10, 70, and/or 170 discussed above in reference to FIGS. 1-4D, except for the differences described herein.

Resilient band coupling member 288 is configured to engage coupling recess 294 of lead 274 in the same manner as discussed above with respect to coupling member 88 and 188. In some examples, resilient band coupling member 288 may be disposed within a channel, such as channel 189 discussed above, or otherwise fixed to a connector of a lead extension. As illustrated in FIG. 5A, in a disengaged configuration, resilient band coupling member 288 may not extending into the channel defined by the connector (not illustrated for clarity). That is, when in the disengaged configuration, resilient band coupling member 288 is configured to allow lead 274 to be inserted or withdrawn from the channel of the connector.

In some examples, as illustrated in FIG. 5B, to disengage resilient band coupling member 288, a clinician may apply pressure to opposing ends of resilient band coupling member 288, as indicated by arrows 202 and 203. In some examples, the hourglass shape of resilient band coupling member 288 may cause resilient band coupling member 288 to move toward a disengaged configuration having a central diameter D1. When the pressure is released, resilient band coupling member 288 may be urged toward an engaged configuration. After the pressure is released, and when resilient band coupling member 288 is aligned with coupling recess 294, as illustrated in FIG. 5C, the elastic response urging resilient band coupling member 288 toward an engaged configuration may cause resilient band coupling member 288 to engage coupling recess 194. In some examples, resilient band coupling member 288 may include an elastic material, nitinol, stainless steel, or MP35N alloy.

Figure 6:
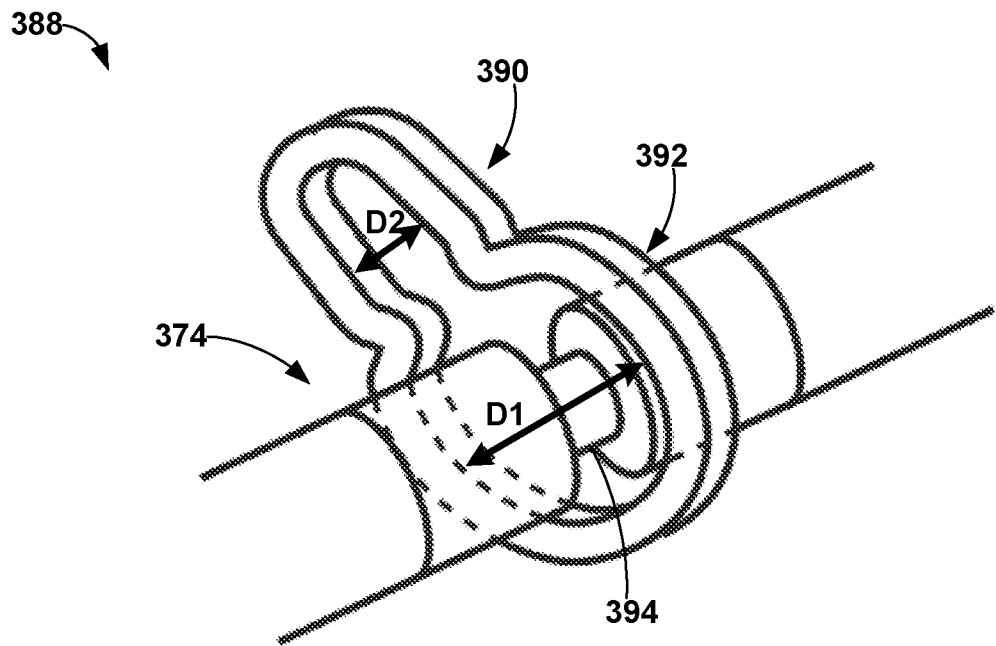
FIG. 6 is a conceptual diagram illustrating a perspective view of an example clip coupling member of medical lead systems.
Figure 7:
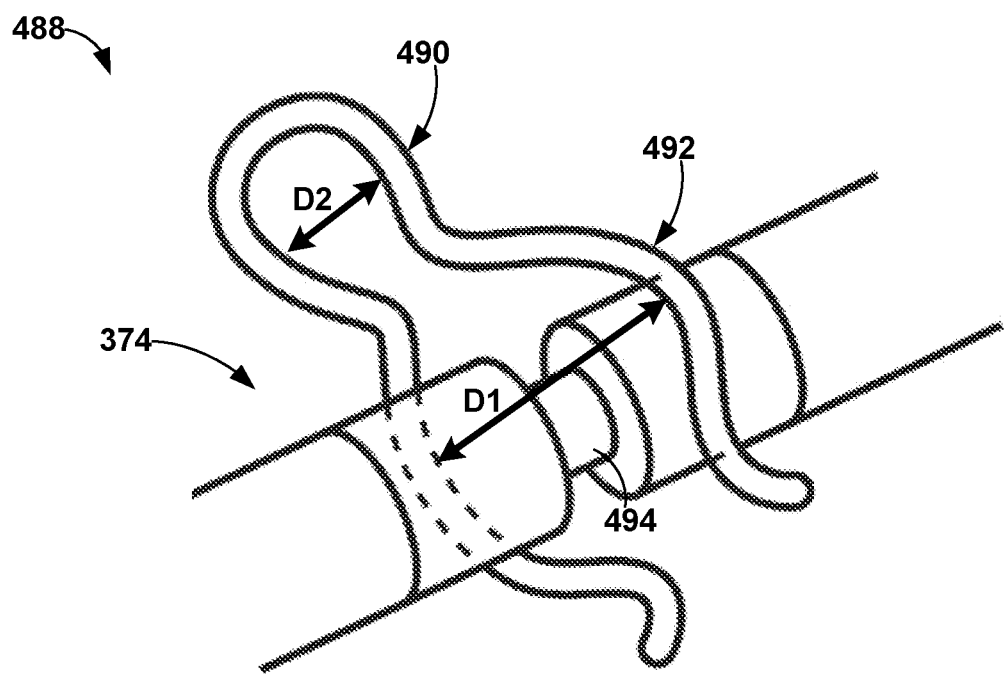
FIG. 7 is a conceptual diagram illustrating a perspective view of an example clip coupling member of medical lead systems.

FIGS. 6 and 7 are conceptual diagrams illustrating perspective views of example clip coupling members 388 and 488 of medical lead systems 370 and 470, respectively. Medical lead systems 370 and 470 may be the same as or substantially similar to medical lead systems 10, 70, 170, and/or 270 discussed above in reference to FIGS. 1-4D, except for the differences described herein. In some examples, coupling members 388 and 488 may be disposed within a channel, such as channel 189 discussed above, or otherwise fixed to a connector of a lead extension.

As illustrated in FIG. 6, clip coupling member 388 includes a close ring clip having a first portion 390 and a second portion 392. First portion 390 has a first diameter D1 that is larger than a diameter of lead 374. When in the disengaged configuration, first portion 390 is positioned within the channel of the connector (not illustrated for clarity), such that lead 374 may be inserted or withdrawn from the channel of the connector. Second portion 392 has a second diameter D2 (smaller than diameter D1) that is smaller than a diameter of lead 374 and allow clip coupling member 388 to engage coupling recess 394. In this way, when in the engaged configuration, second portion 392 is positioned within the channel of the connector, such that lead 374 is secured in the axial direction relative to the lead extension.

As illustrated in FIG. 7, clip coupling member 488 includes an open horseshoe clip having a first portion 490 and a second portion 492. First portion 490 has a first diameter D1 that is larger than a diameter of lead 474. When in the disengaged configuration, first portion 490 is positioned within the channel of the connector (not illustrated for clarity), such that lead 474 may be inserted or withdrawn from the channel of the connector. Second portion 492 has a second diameter D2 (smaller than diameter D1) that is smaller than a diameter of lead 474 and allow clip coupling member 488 to engage coupling recess 494. In this way, when in the engaged configuration, second portion 492 is positioned within the channel of the connector, such that lead 474 is secured in the axial direction relative to the lead extension.

Figure 8A:
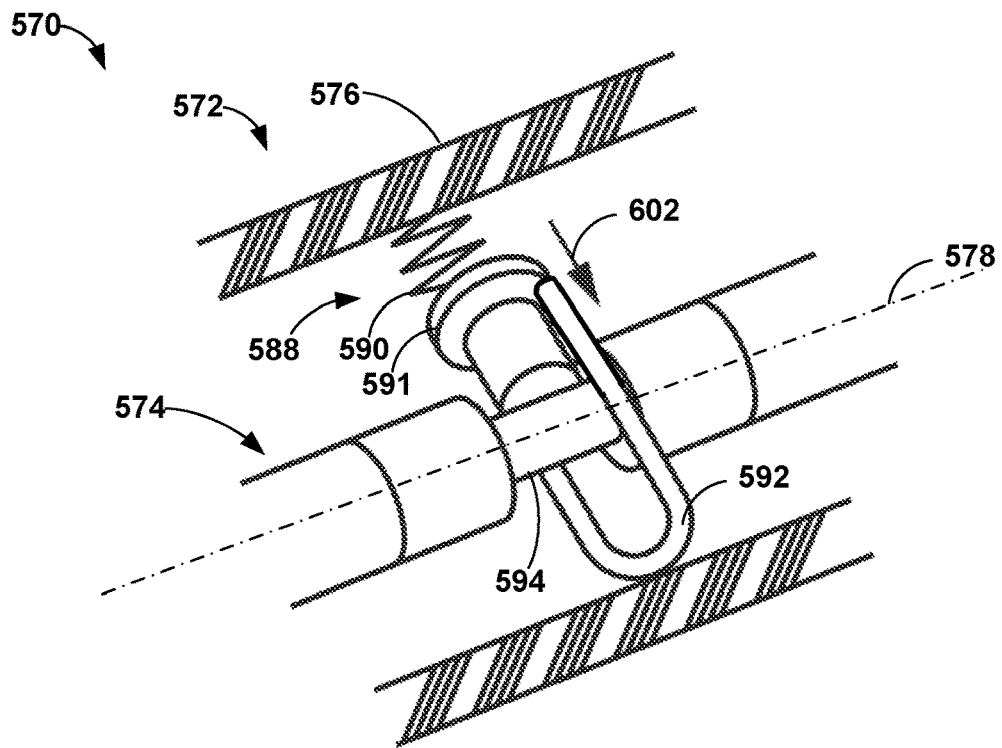
FIGS. 8A and 8B are conceptual diagrams illustrating plan views of an example coupling member of a medical lead system that is biased to an engage configuration.
Figure 8B:
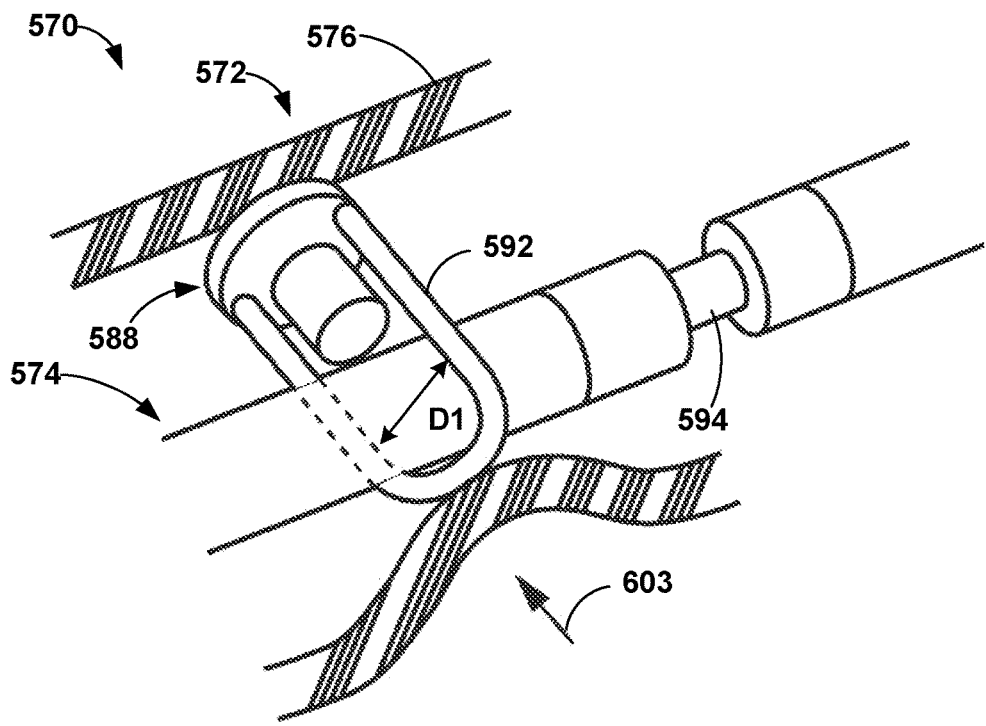

In some examples, the coupling member of the lead extension may be biased to an engage configuration. FIGS. 8A and 8B are conceptual diagrams illustrating plan views of an example coupling member 588 of a medical lead system 570 that is biased to an engage configuration. Medical lead systems may be the same as or substantially similar to medical lead systems 10, 70, 170, 270, 370, and/or 470 discussed above in reference to FIGS. 1-7, except for the differences described herein.

Medical lead system 570 includes lead extension 572 and lead 574. Lead extension 573 includes coupling member 588. Coupling member 588 includes a biasing member 590 extending from a radially interior surface of connector 576. Biasing member 590 may include a resilient material configured to be biased toward a selected configuration, such as the engaged configuration of coupling member 588. For example, biasing member 590 includes a coil spring. In some examples, biasing member 590 may include a leaf spring, a volute spring, an elastic polymer, or other elastic structure configured to store mechanical energy. Biasing member 590 is coupled to displaceable protrusion 591. In the example illustrated in FIGS. 8A and 8B, displaceable protrusion 591 includes a cylindrical base plate coupled to biasing member and a cylindrical retention member extending from the base plate and configured to engage recess 594 of lead 574. Biasing member 590 is configured to urge displaceable protrusion 591 radially inward toward longitudinal axis 578.

In some examples, coupling member 588 may include a guide member 592. Guide member 592 may be configured to align displaceable protrusion 591 with coupling recess 594. For example, guide member 592 may define a u-shaped wire. The respective ends of the u-shaped bar may extend from the base plate of displaceable protrusion 591 and define a diameter D1 that is greater than a diameter of lead 574. In this way, lead 574 may extend through the aperture defined by guide member 592. In some examples, to move coupling member 588 toward a disengaged configuration, a clinician may apply a force, indicated by arrow 603, to guide member 592. After releasing the force, biasing member 590 may urge displaceable protrusion toward the engaged configuration such that when coupling recess 594 of lead 524 is aligned with displaceable protrusion 591, displaceable protrusion 591 may automatically engage coupling recess 594.

Figure 9A:
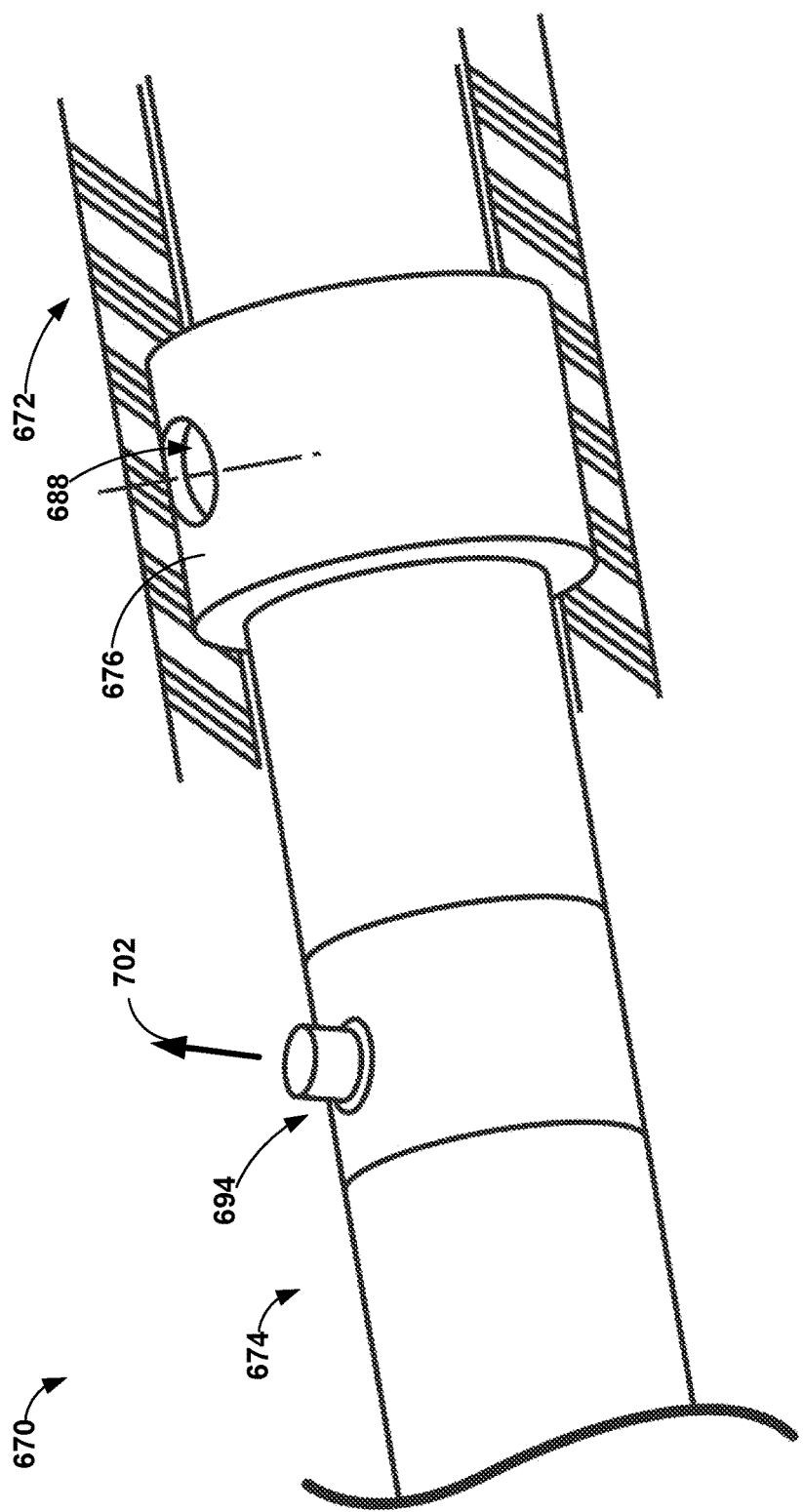
FIG. 9A is a conceptual diagram illustrating a perspective view of an example medical lead system that includes a lead extension having a connector defining a recess that is configured to be engaged with a coupling member of a lead.
Figure 9B:
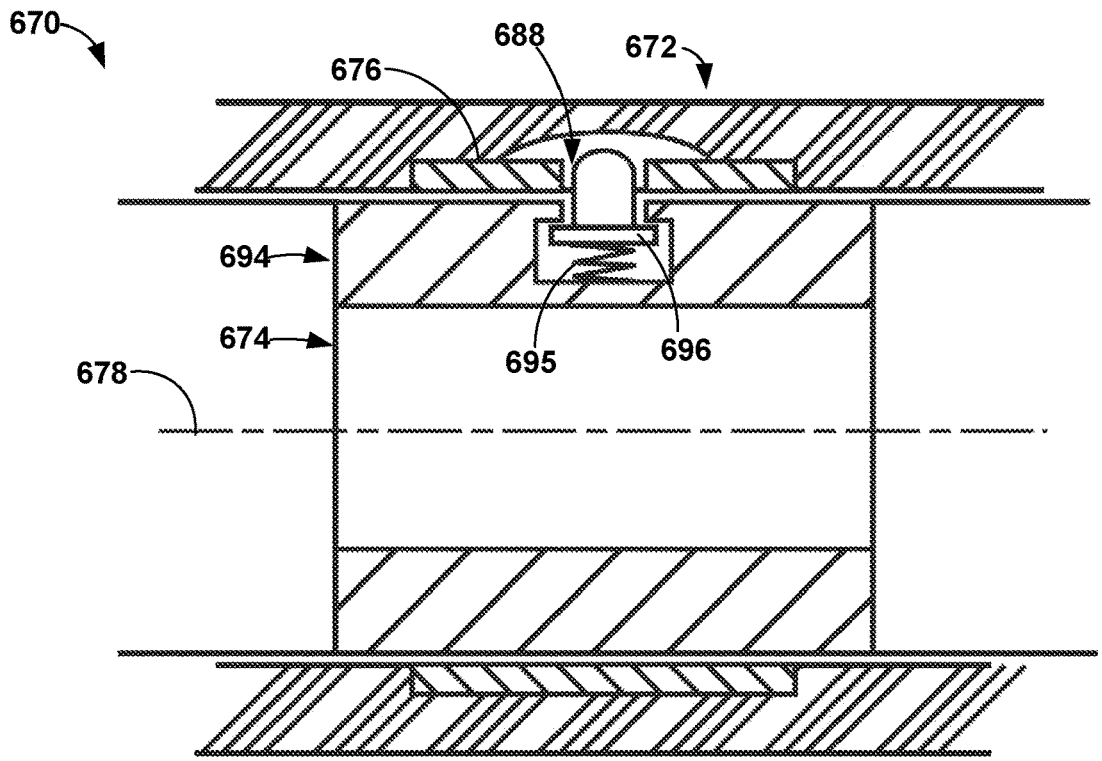
FIGS. 9B and 9C are axial cross sectional views of the engaged and disengaged configurations, respectively, of the medical lead system illustrated in FIG. 9A.
Figure 9C:
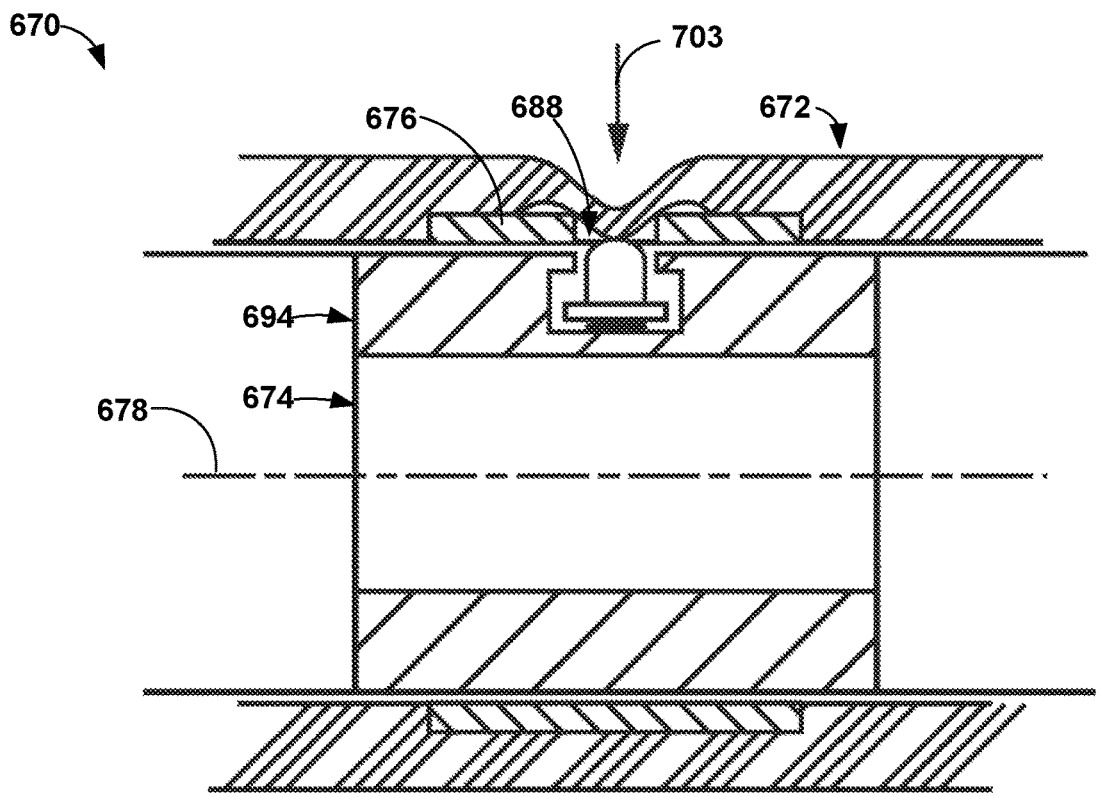

As discussed above in reference to FIG. 3A, in some examples, the coupling member of a lead extension may define a recess and the corresponding coupling member of a lead may include a displaceable protrusion. FIG. 9A is a conceptual diagram illustrating a perspective view of an example medical lead system 670 that includes a lead extension 672 having a connector 676 defining a coupling recess 688 that is configured to be engaged with a coupling member 694 of a lead 674. FIGS. 9B and 9C are axial cross sectional views of the engaged and disengaged configurations, respectively, of medical lead system 670. Medical lead system 670 may be the same as or substantially similar to medical lead systems 10, 70, 170, 270, 370, 470, and/or 570 discussed above in reference to FIGS. 1-8B, except for the differences described herein.

Coupling member 694 may include biasing member 695 configured to bias a displaceable protrusion 696 of coupling member 694 toward an engaged configuration, e.g., as indicated by arrow 702. Biasing member 695 may be the same or substantially similar to biasing member 590 discussed above in reference to FIGS. 8A and 8B. In the engaged configuration, displaceable protrusion 696 may extend into coupling recess to mechanically coupled lead extension 672 to lead 674. Although illustrated as an aperture, in other example, coupling recess 688 may define one or more partial or fully circumferential channels enabling rotation of lead extension 672 about axis 678. In some examples, to move coupling member 694 toward a disengaged configuration, a clinician may apply a force, indicated by arrow 703, to displaceable protrusion 696. After releasing the force, biasing member 695 may urge displaceable protrusion 696 toward the engaged configuration such that when coupling recess 688 of lead extension 672 is aligned with displaceable protrusion 696, displaceable protrusion 696 may automatically engage coupling recess 688.

Figure 10:
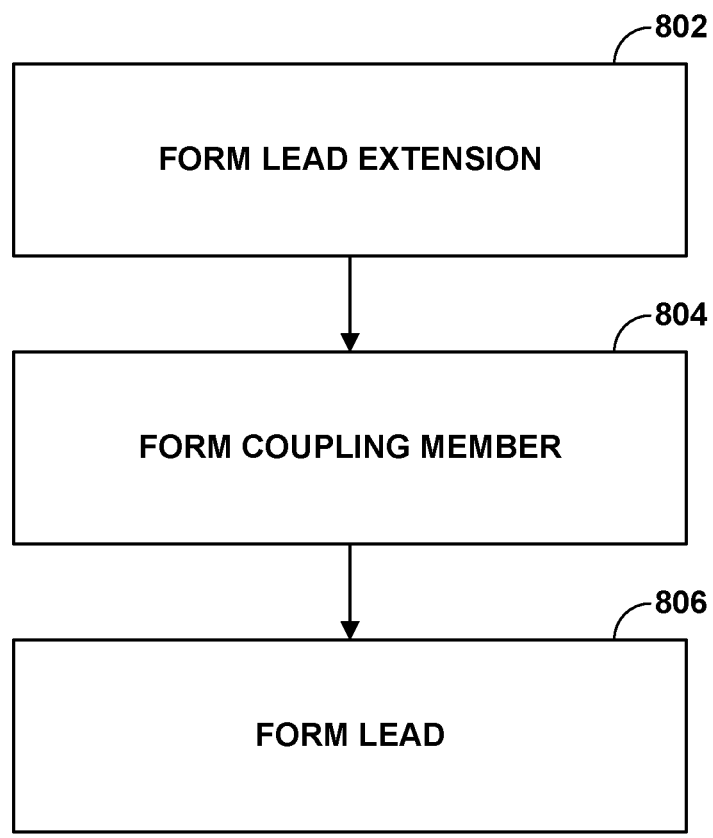
FIG. 10 is a flow diagram of an example technique for manufacturing an implantable medical lead.

FIG. 10 is a flow diagram of an example technique for manufacturing an medical lead system. Although described with respect to medical lead system 170 as illustrated in reference to FIGS. 3A-3C, in some examples, the technique may be used to manufacture other medical lead systems, such as any of medical lead systems 70, 270, 370, 470, 570, and/or 670. Moreover, any of medical lead systems 70, 170, 270, 370, 470, 570, and/or 670 may be manufactured using different techniques.

The technique illustrated in FIG. 10 includes forming lead extension 72 including elongate body 80 and connector 76 (802). In some examples, connector 76 may be integrally formed with elongate body 80. For example, a jacket or an insulative material of elongate body 80 formed, e.g., by injection molding, together with connector 76. In some examples, elongate body 80 and connector 76 may be formed separately and coupled, for example, using an adhesive, ultrasonic welding, thermal welding, or the like.

The technique also includes forming coupling member 88 (804). In examples in which coupling member 88 includes a pin, forming coupling member 88 may include molding the pin. In examples in which coupling member 88 includes two or more components, e.g., a biased member and displaceable protraction, forming coupling member 88 may include separately forming the two or more components and assembling them to define coupling member 88.

In some examples, the technique may optionally include positioning coupling member 88 within connector 76. For example, the technique may include positioning coupling member 88 within a cavity defined by connector 76 and/or joining at least a portion of coupling member 88 to at least a portion of connector 76.

In some examples, the technique may optionally include forming lead 74 (806). In some examples, forming lead 74 may include elongate body 90 to define coupling recess 94. In some examples, forming lead 74 may include machining or cutting elongate body 90 to define coupling recess 94.

Although described with respect to forming lead extension 72 including connector 76, in other examples, as discussed above, lead 74 may be formed to include connector 76. The technique illustrated in FIG. 10 may be performed in any suitable order.

The above features and techniques are examples. Any suitable techniques may be used to fabricate the structures described herein and may vary based on the particular materials employed for the respective components.

Figure 11:
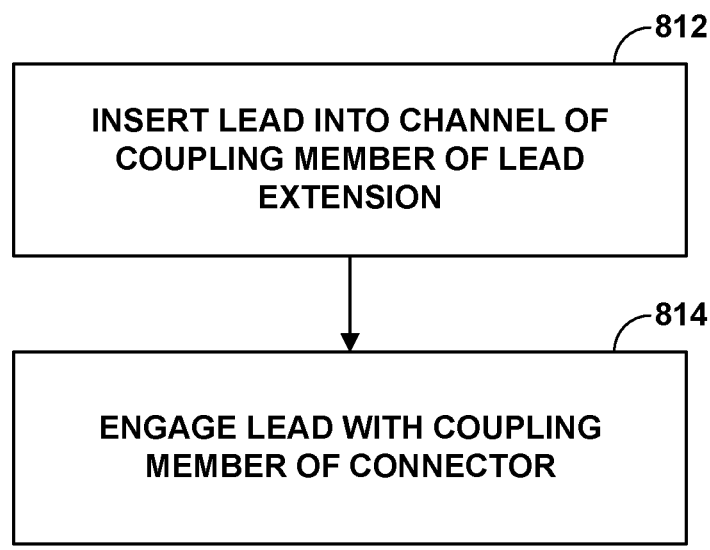
FIG. 11 is a flow diagram of an example technique for coupling a lead extension to a lead.

FIG. 11 is a flow diagram of an example technique for coupling a lead extension to a lead. Although described with respect to medical lead system 170 as illustrated in reference to FIGS. 3A-3C, in some examples, the technique may be used to manufacture other medical lead systems, such as any of medical lead systems 70, 270, 370, 470, 570, and/or 670. Moreover, any of medical lead systems 70, 170, 270, 370, 470, 570, and/or 670 may be used with different techniques.

The technique illustrated in FIG. 11 includes inserting proximal end 92 of lead 74 into channel 84 of connector 76 of lead extension 72 (812). The technique illustrated in FIG. 11 also includes mechanically engaging, by coupling member 88 of connector 76, a corresponding coupling member (e.g., coupling recess 94) of lead 74 to secure lead extension 72 to lead 74 at least in the axial direction relative to longitudinal axis 78 (814).

The above features and techniques are examples. Any suitable techniques may be used to mechanically couple a lead and/or lead extension to the described connectors and may vary based on the particular configurations of the lead, lead extension, and/or connector employed.

The following clauses illustrate example subject matter described herein.

Clause 1. A medical lead system comprising: a first lead portion comprising a first elongate body extending along a longitudinal axis from a distal end to a proximal end and defining a coupling recess; and a second lead portion comprising: a second elongate body extending along the longitudinal axis from a distal end to a proximal end; and a connector defining a channel configured to receive the proximal end of the first lead portion and comprising a coupling member configured to, when the first lead portion is inserted into the channel, mechanically engage the coupling recess to secure the first lead portion to the second lead portion at least in an axial direction relative to the longitudinal axis, and wherein one of the first lead portion or the second lead portion carries one or more electrodes.

Clause 2. The medical lead system of clause 1, wherein the coupling recess defines a recess surface radially offset inward relative to a major surface of the elongate body of the first lead portion, and wherein the coupling member comprises a displaceable protrusion configured to mechanically engage at least a portion of the coupling recess.

Clause 3. The medical lead system of clause 1 or 2, wherein the coupling member comprises at least one of a pin, button, clip, band, spring, or hook.

Clause 4. The medical lead system of any one of clauses 1 through 3, wherein the coupling member is disposed within a cavity defined by a body of the connector.

Clause 5. The medical lead system of any one of clauses 1 through 4, wherein the coupling member comprises a resilient material or a biased member configured to urge the coupling member toward an engaged configuration of the coupling member.

Clause 6. The medical lead system of any one of clauses 1 through 5, wherein the proximal end of the first lead portion comprises at least one electrical terminal extending about the longitudinal axis, wherein the one or more electrodes are electrically coupled to the electrical terminal, and wherein the connector further comprises at least one electrical contact disposed on a surface of the connector defining the channel and configured to, when the first lead portion is inserted into the channel, electrically couple to the electrical terminal of the first lead portion.

Clause 7. The medical lead system of clause 6, wherein the electrical terminal of the first lead portion comprises a plurality of electrical terminals, each respective electrical terminal disposed at different respective positions on the first lead portion body relative to the longitudinal axis, and wherein the electrical contact of the second lead portion comprises a plurality of electrical contacts, each respective electrical contact disposed at different respective positions on the channel such that each respective electrical terminal of the first lead portion body electrically couples to a respective electrical contact when the first lead portion is mechanically secured within the channel.

Clause 8. The medical lead system of any one of clauses 1 through 7, wherein the first lead portion comprises a medical lead, and wherein the second lead portion comprises a medical lead extension.

Clause 9. The medical lead system of any one of clauses 1 through 8, wherein the proximal end of the second lead portion is configured to electrically couple to an implantable medical device (IMD).

Clause 10. A medical lead system comprising: a first lead portion comprising a first elongate body extending along a longitudinal axis from a distal end to a proximal end and coupling member; and a second lead portion comprising a second elongate body extending along the longitudinal axis from a distal end to a proximal end, wherein the distal end of the second lead portion comprises a connector defining a channel configured to receive the proximal end of the first lead portion, wherein the connector defines a coupling recess, and wherein the coupling member is configured to, when the first lead portion is inserted into the channel, mechanically engage the coupling recess to secure the first lead portion to the second lead portion at least in an axial direction relative to the longitudinal axis, and wherein one of the first lead portion or the second lead portion carries one or more electrodes.

Clause 11. The medical lead system of clause 10, wherein the coupling recess defines a recess surface radially offset outward relative to the longitudinal axis, and wherein the coupling member comprises a displaceable protrusion configured to mechanically engage at least a portion of the coupling recess.

Clause 12. The medical lead system of clause 10 or 11, wherein the coupling member comprises at least one of a pin, button, clip, band, spring, or hook.

Clause 13. The medical lead system of any one of clauses 10 through 12, wherein the coupling member is disposed within a cavity defined by the elongate body of the first lead portion.

Clause 14. The medical lead system of any one of clauses 10 through 13, wherein the coupling member comprises a resilient material or a biased member configured to urge the coupling member toward an engaged configuration of the coupling member.

Clause 15. The medical lead system of any one of clauses 10 through 14, wherein the proximal end of the first lead portion comprises at least one electrical terminal extending about the longitudinal axis, wherein the one or more electrodes are electrically coupled to the electrical terminal, and wherein the connector further comprises at least one electrical contact disposed on a surface of the connector defining the channel and configured to, when the first lead portion is inserted into the channel, electrically couple to the electrical terminal of the first lead portion.

Clause 16. The medical lead system of clause 15, wherein the electrical terminal of the first lead portion comprises a plurality of electrical terminals, each respective electrical terminal disposed at different respective positions on the first lead portion body relative to the longitudinal axis, and wherein the electrical contact of the second lead portion comprises a plurality of electrical contacts, each respective electrical contact disposed at different respective positions on the channel such that each respective electrical terminal of the first lead portion body electrically couples to a respective electrical contact when the first lead portion is mechanically secured within the channel.

Clause 17. The medical lead system of any one of clauses 10 through 16, wherein the first lead portion comprises a medical lead, and wherein the second lead portion comprises a medical lead extension.

Clause 18. The medical lead system of any one of clauses 10 through 17, wherein the proximal end of the second lead portion is configured to electrically couple to an implantable medical device (IMD).

Clause 19. A medical lead system comprising an elongate body extending along a longitudinal axis from a distal end to a proximal end, wherein the elongate body defines a coupling recess, wherein the proximal end of the elongate body is configured to be received in a channel defined by a connector extending from a distal end of a medical lead extension, and wherein the coupling recess, when the proximal end of the elongate body is inserted into the channel of the lead extension, is configured to receive a coupling member of the lead extension to mechanically secure the elongate body to the lead extension at least in an axial direction relative to the longitudinal axis.

Clause 20. The medical lead system of clause 19, further comprising the lead extension.

Clause 21. A medical lead system comprising: an elongate body extending along the longitudinal axis from a distal end to a proximal end; and a connector extending from the distal end of the elongate body, wherein the connector defines a channel configured to receive a proximal end of a medical lead, wherein the connector comprises a coupling member configured to, when the proximal end of the lead is inserted into the channel, mechanically engage a coupling recess defined by the proximal end of the lead to secure the lead to the lead extension at least in an axial direction relative to the longitudinal axis.

Clause 22. The medical lead system of clause 21, further comprising the lead.

Various aspects of the disclosure have been described. These and other aspects are within the scope of the following claims.

What is claimed is:

1. A medical lead system comprising:
    a first lead portion comprising a first elongate body extending along a longitudinal axis from a distal end to a proximal end and defining a coupling recess, the coupling recess extending around an entire circumference of the first elongate body, wherein the coupling recess is disposed distal of one or more electrical terminals on the proximal end of the first lead portion, and wherein the coupling recess is disposed proximal of one or more electrodes disposed on the distal end of the first lead portion; and
    a second lead portion comprising:
        a second elongate body extending along the longitudinal axis from a distal end to a proximal end; and
        a connector defining a channel configured to receive the proximal end of the first lead portion and comprising a coupling member configured to, when the first lead portion is inserted into the channel, mechanically engage the coupling recess to secure the first lead portion to the second lead portion at least in an axial direction relative to the longitudinal axis.

2. The medical lead system of claim 1, wherein the coupling recess defines a recess surface radially offset inward relative to a major surface of the elongate body of the first lead portion, and wherein the coupling member comprises a displaceable protrusion configured to mechanically engage at least a portion of the coupling recess.

3. The medical lead system of claim 1, wherein the coupling member comprises at least one of a pin, button, clip, band, spring, or hook.

4. The medical lead system of claim 1, wherein the coupling member is disposed within a cavity defined by a body of the connector.

5. The medical lead system of claim 1, wherein the coupling member comprises a resilient material or a biased member configured to urge the coupling member toward an engaged configuration of the coupling member.

6. The medical lead system of claim 1, wherein the proximal end of the first lead portion comprises at least one electrical terminal extending about the longitudinal axis, wherein the one or more electrodes are electrically coupled to the electrical terminal, and wherein the connector further comprises at least one electrical contact disposed on a surface of the connector defining the channel and configured to, when the first lead portion is inserted into the channel, electrically couple to the electrical terminal of the first lead portion.

7. The medical lead system of claim 6, wherein the electrical terminal of the first lead portion comprises a plurality of electrical terminals, each respective electrical terminal disposed at different respective positions on the first lead portion body relative to the longitudinal axis, and wherein the electrical contact of the second lead portion comprises a plurality of electrical contacts, each respective electrical contact disposed at different respective positions on the channel such that each respective electrical terminal of the first lead portion body electrically couples to a respective electrical contact when the first lead portion is mechanically secured within the channel.

8. The medical lead system of claim 1, wherein the first lead portion comprises a medical lead, and wherein the second lead portion comprises a medical lead extension.

9. The medical lead system of claim 1, wherein the proximal end of the second lead portion is configured to electrically couple to an implantable medical device (IMD).

10. A medical lead system comprising:
a first lead portion comprising a first elongate body extending along a longitudinal axis from a distal end to a proximal end and coupling member; and
a second lead portion comprising a second elongate body extending along the longitudinal axis from a distal end to a proximal end, wherein the distal end of the second lead portion comprises a connector defining a channel configured to receive the proximal end of the first lead portion, wherein the connector defines a coupling recess, and wherein the coupling member is configured to, when the first lead portion is inserted into the channel, mechanically engage the coupling recess to secure the first lead portion to the second lead portion at least in an axial direction relative to the longitudinal axis, and
wherein the connector comprises one or more electrical contacts disposed proximal of the coupling recess, and
wherein one of the first lead portion or the second lead portion carries one or more electrodes.

11. The medical lead system of claim 10, wherein the coupling recess defines a recess surface radially offset outward relative to the longitudinal axis, and wherein the coupling member comprises a displaceable protrusion configured to mechanically engage at least a portion of the coupling recess.

12. The medical lead system of claim 10, wherein the coupling member comprises at least one of a pin, button, clip, band, spring, or hook.

13. The medical lead system of claim 10, wherein the coupling member is disposed within a cavity defined by the elongate body of the first lead portion.

14. The medical lead system of claim 10, wherein the coupling member comprises a resilient material or a biased member configured to urge the coupling member toward an engaged configuration of the coupling member.

15. The medical lead system of claim 10, wherein the proximal end of the first lead portion comprises at least one electrical terminal extending about the longitudinal axis, wherein the one or more electrodes are electrically coupled to the electrical terminal, and wherein the one or more electrical contacts are disposed on a surface of the connector defining the channel and configured to, when the first lead portion is inserted into the channel, electrically couple to the electrical terminal of the first lead portion.

16. The medical lead system of claim 15, wherein the electrical terminal of the first lead portion comprises a plurality of electrical terminals, each respective electrical terminal disposed at different respective positions on the first lead portion body relative to the longitudinal axis, and wherein the electrical contact of the second lead portion comprises a plurality of electrical contacts, each respective electrical contact disposed at different respective positions on the channel such that each respective electrical terminal of the first lead portion body electrically couples to a respective electrical contact when the first lead portion is mechanically secured within the channel.

17. The medical lead system of claim 10, wherein the first lead portion comprises a medical lead, and wherein the second lead portion comprises a medical lead extension.

18. The medical lead system of claim 10, wherein the proximal end of the second lead portion is configured to electrically couple to an implantable medical device (IMD).

19. A medical lead system comprising an elongate body extending along a longitudinal axis from a distal end to a proximal end,
wherein the elongate body defines a coupling recess, the coupling recess extending around the entire circumference of the elongate body,
wherein the coupling recess is disposed distal of one or more electrical terminals on a proximal end of the elongate body, and wherein the coupling recess is disposed proximal of one or more electrodes disposed on a distal end of the elongate body, and
wherein the proximal end of the elongate body is configured to be received in a channel defined by a connector extending from a distal end of a medical lead extension, and
wherein the coupling recess, when the proximal end of the elongate body is inserted into the channel of the lead extension, is configured to receive a coupling member of the lead extension to mechanically secure the elongate body to the lead extension at least in an axial direction relative to the longitudinal axis.

20. The medical lead system of claim 19, further comprising the lead extension.

21. A medical lead system comprising:
an elongate body extending along the longitudinal axis from a distal end to a proximal end; and
a connector extending from the distal end of the elongate body, wherein the connector defines a channel configured to receive a proximal end of a medical lead, wherein the connector comprises a coupling member configured to, when the proximal end of a lead is inserted into the channel, mechanically engage a coupling recess defined by the proximal end of the lead to secure the lead to the elongate body at least in an axial direction relative to the longitudinal axis, wherein the coupling recess extends around the entire circumference of the lead, and wherein the coupling member is disposed distal of one or more electrical terminals on the distal end of the elongate body, the coupling member positioned to mechanically engage the coupling recess disposed between one or more electrical terminals at the proximal end of the lead and one or more electrodes disposed at a distal ed of the lead.

22. The medical lead system of claim 21, further comprising the lead.

* * * * *